(12) United States Patent  
Stephenson

(10) Patent No.: US 9,025,824 B2  
(45) Date of Patent: May 5, 2015

(54) SYSTEMS AND METHODS FOR EVALUATING PHYSICAL PERFORMANCE

(71) Applicant: Movement Training Systems LLC, Littleton, CO (US)

(72) Inventor: Vincent Ned Stephenson, Littleton, CO (US)

(73) Assignee: Movement Training Systems LLC, Littleton, CO (US)

( * ) Notice: Subject to any disclaimer, the term of this patent is extended or adjusted under 35 U.S.C. 154(b) by 0 days.

(21) Appl. No.: 13/843,211

(22) Filed: Mar. 15, 2013

(65) Prior Publication Data

US 2013/0223707 A1    Aug. 29, 2013

Related U.S. Application Data

(63) Continuation-in-part of application No. 13/520,790, filed as application No. PCT/US2011/063801 on Dec. 7, 2011, now Pat. No. 8,428,357.

(60) Provisional application No. 61/420,524, filed on Dec. 7, 2010.

(51) Int. Cl.
*G06K 9/00* (2006.01)
*A63B 24/00* (2006.01)

(52) U.S. Cl.
CPC ........ *G06K 9/00362* (2013.01); *A63B 24/0003* (2013.01)

(58) Field of Classification Search
USPC ......... 382/100, 103, 107, 159, 181, 190, 195, 382/203; 348/135, 143, 157, 169–172
See application file for complete search history.

(56) References Cited

U.S. PATENT DOCUMENTS

| 6,537,076 B2 | 3/2003 | McNitt et al. |
| 6,567,536 B2 * | 5/2003 | McNitt et al. ................. 382/107 |

(Continued)

FOREIGN PATENT DOCUMENTS

| KR | 10-0037961 A | 4/2010 |
| KR | 10-0772497 | 11/2011 |

(Continued)

OTHER PUBLICATIONS

International Search Report for International Application No. PCT/US2014/030520 dated Jul. 3, 2014, 11 pages.

(Continued)

*Primary Examiner* — Anand Bhatnagar
(74) *Attorney, Agent, or Firm* — Procopio, Cory, Hargreaves & Savitch LLP; Noel C. Gillespie

(57) ABSTRACT

Systems and methods are provided for evaluating and correcting physical performance of an activity by a human. A user performing one or more physical activities may be evaluated based on criteria relating to their movement, such as strength and technique. The user's performance in relation to these criteria is then rated, and the values for the criteria are combined to provide an overall performance score. The performance score is used to determine a user's overall readiness and ability to perform the physical activity which was evaluated or an overall ability to perform physical activities. Performance scores for more than one physical activity may be combined to provide an overall performance ready score that captures the person's overall physical ability. Comparisons of performance scores over time may provide information as to whether a user is improving, and could be applied to evaluating physical rehabilitations from injuries.

9 Claims, 21 Drawing Sheets

(56) References Cited

U.S. PATENT DOCUMENTS

| | | | |
|---|---|---|---|
| 6,687,386 B1 | 2/2004 | Ito et al. | |
| 7,264,554 B2* | 9/2007 | Bentley | 473/222 |
| 7,283,647 B2* | 10/2007 | McNitt | 382/107 |
| 7,791,808 B2* | 9/2010 | French et al. | 359/630 |
| 7,857,708 B2 | 12/2010 | Ueda et al. | |
| 8,139,822 B2* | 3/2012 | Selner | 382/107 |
| 8,175,326 B2* | 5/2012 | Siegel | 382/100 |
| 8,233,721 B2 | 7/2012 | Wagg | |
| 8,235,870 B2 | 8/2012 | Hamilton | |
| 8,335,345 B2* | 12/2012 | White et al. | 382/103 |
| 8,428,357 B2* | 4/2013 | Stephenson | 382/181 |
| 2002/0176603 A1 | 11/2002 | Bauer | |
| 2002/0187846 A1 | 12/2002 | Funk | |
| 2005/0223799 A1 | 10/2005 | Murphy | |
| 2005/0271279 A1 | 12/2005 | Fujimura et al. | |
| 2006/0003300 A1 | 1/2006 | Davis | |
| 2008/0094472 A1* | 4/2008 | Ayer et al. | 348/157 |
| 2008/0119763 A1* | 5/2008 | Wiener | 600/587 |
| 2008/0136907 A1* | 6/2008 | Karikko et al. | 348/143 |
| 2008/0219509 A1* | 9/2008 | White et al. | 382/107 |
| 2008/0269644 A1* | 10/2008 | Ray | 600/587 |
| 2008/0319349 A1 | 12/2008 | Zilberman | |
| 2009/0141933 A1 | 6/2009 | Wagg | |
| 2009/0148000 A1 | 6/2009 | Madsen et al. | |
| 2009/0220124 A1* | 9/2009 | Siegel | 382/103 |
| 2009/0298650 A1 | 12/2009 | Kutliroff | |
| 2010/0041498 A1 | 2/2010 | Adams | |
| 2010/0177933 A1* | 7/2010 | Willmann et al. | 382/107 |
| 2011/0052005 A1* | 3/2011 | Selner | 382/103 |
| 2011/0112808 A1* | 5/2011 | Anderson et al. | 703/2 |

FOREIGN PATENT DOCUMENTS

| | | |
|---|---|---|
| WO | 2007059301 A2 | 5/2007 |
| WO | 2012078795 A1 | 6/2012 |

OTHER PUBLICATIONS

International Search Report for International Application No. PCT/US2011/063801, dated Apr. 30, 2012, 7 pages.

Samenien et al., "The Evaluation of the Rehabilitation Effects on Cognitive Dysfunction and Changes in Psychomotor Reactions in Stroke Patients", Medicina (Kaunas), vol. 44, No. 11. pp. 860-870 (2008).

Canadian Patent Office Action dated Sep. 9, 2013, for Application No. 2,819,067, 7 pages.

Recovering Human Body Configurations Using Pairwise Constraints Between Parts, Xiaofeng Ren; Computer Vision, 2005. ICCV 2005. Tenth IEEE International Conference on (vol. 1); Oct. 17-21, 2005; pp. 824-831 vol. 1; ISSN: 1550-5400; ISBN: 0-7695-2334-X.

European Search Report for Application No. 11846995.6, dated Mar. 17, 2014, 4 pages.

* cited by examiner

FIG. 22

Overall Performance Ready (Comprises all components above and measures readiness to perform athletically)

| Name | Performance Ready(Beginning) | Performance Ready(Current) | % Change |
|---|---|---|---|
|  | 26 | 26 | 0 |
|  | 48.2 | 48.2 | 0 |
|  | 50.2 | 50.3 | 0 |
|  | 40 | 40 | 0 |
|  | 27.7 | 27.7 | 0 |
|  | 40.6 | 40.6 | 0 |
|  | 20.6 | 20.6 | 0 |
|  | 28.1 | 28.1 | 0 |
|  | 36.6 | 36.6 | 0 |
|  | 38.8 | 38.8 | 0 |
|  | 55.5 | 55.5 | 0 |
|  | 30.9 | 30.9 | 0 |
|  | 30.5 | 30.5 | 0 |
|  | 35.5 | 35.5 | 0 |

FIG. 23

Message Board

| From Name | Id Code | Message | Date | Player | Send | Delete |
|---|---|---|---|---|---|---|
| Debi | brown953 | Great use of feet to get around goal | 02/19/13 19:26 | lax022 | ◎ | ◎ |
| Debi | brown953 | On the drill where they hit the pad | 02/19/13 19:19 | | ◎ | ◎ |

Submit

FIG. 24

SYSTEMS AND METHODS FOR EVALUATING PHYSICAL PERFORMANCE

PRIORITY CLAIM

This application claims priority to pending U.S. application Ser. No. 13/520,790, filed Jul. 5, 2012, which is a 371 national stage application of PCT International Application No. PCT/US2011/6380, filed Dec. 7, 2011, which claims priority to U.S. Provisional Application No. 61/420,524, filed Dec. 7, 2010, now abandoned.

BACKGROUND

1. Technical Field

The embodiments described herein are related to systems and methods for performance training based on position tracking, movement mechanics and functional strength development, as well as systems and methods for evaluating physical performance.

2. Related Art

Athletes often employ various training systems and/or methods to improve athletic performance. Such training systems and/or methods can be divided into at least two groups. One such group includes training systems and methods which are primarily aimed at improving or maintaining the physical conditioning of the athlete. Thus, such athletic conditioning training systems and methods are generally configured to improve or maintain the strength and stamina of the athlete. An example of a conditioning training system is a set of weights for weightlifting. Similarly, an example of a conditioning training method is a method of using such weights to increase strength and stamina of an athlete.

The other of the two groups of athletic training systems and methods includes systems and methods that are aimed primarily at improving or maintaining an athletic technique. As used herein, "technique" refers to the manner in which an athlete executes an athletic maneuver such as running, jumping, throwing, and the like. Thus, such athletic technique training systems and methods are generally configured to improve or maintain an athlete's form, body positioning, and movement while performing an athletic maneuver.

The technique possessed by an athlete can be as important, if not more important, than the strength and/or stamina of the athlete. For example, assuming all other factors are equal, an athlete of inferior conditioning and stamina who possesses superior technique can sometimes out-perform an athlete of superior conditioning and stamina who possesses inferior technique. Superior athletic technique, then, can be a determining factor in the outcome of any given athletic event such as a game or other competition.

The training systems which improve or maintain an athletic technique primarily use physical sensors which are placed on the body of the athlete in order to measure the athlete's movement and position. The sensors may provide visual tracking of the movement and position to an image capture device or provide actual data on movement and position via components within the sensors which are equipped to measure movement and position. However, the use of these sensors limits the applicability of these training systems to environments where the sensors can be attached to the user or where specialized equipment is available to read the data generated by the sensors. The training system may require a specially-designed space, thus limiting the applicability to athletes who are engaged in normal training that is on a field, outdoors or with a team.

SUMMARY

Systems and methods are provided for evaluating and correcting physical performance of an activity by a human. A user performing one or more physical activities may be evaluated based on criteria relating to their movement, such as strength and technique. The user's performance in relation to these criteria is then rated, and the values for the criteria are combined to provide an overall performance score. The performance score is used to determine a user's overall readiness and ability to perform the physical activity which was evaluated or an overall ability to perform physical activities. Performance scores for more than one physical activity may be combined to provide an overall performance ready score that captures the person's overall physical ability. Comparisons of performance scores over time may provide information as to whether a user is improving or regressing, and could be specifically applied to evaluating physical rehabilitations from injuries or targeted types of training activities and techniques. Corrections to a user's technique can also be offered based on the specific rating the user received with regard to technique.

In one embodiment of the invention, a method of assessing performance readiness of a human comprises: receiving at least one image of a user performing a physical activity; evaluating a technique of the user's performance and determining a technique score based on the evaluation; determining a strength score based on the user's measured strength during the physical activity; combining the technique score and the strength score to generate a performance ready score; and displaying the performance ready score on a display.

In another embodiment of the invention, a method of assessing a physical rehabilitation process of a human comprises: generating a first performance ready score for a user, wherein the performance ready scores measures an ability of a user to perform a physical activity; generating a second performance ready score for the user after the user has been physically impaired or injured; comparing the first performance ready score and the second performance ready score to determine a difference between the first performance ready score and the second performance ready score; and determining a progress of a rehabilitation process of the user based on the determined difference.

Systems and methods for tracking and correcting a position or movement of the human body are presented. An image capture device such as a still camera or video camera captures an image or video of a human body in a selected position or sequence of positions relating to a movement. The position or movement may relate to a physical activity, such as running, jumping, throwing or swinging. The image is then presented to a user on a display, where the user may select one or more positions of the human body for analysis. Upon selecting a position, an angle of the position is determined and then compared to a desired angle determined through specific biomechanical measurements. The difference between the two angles is calculated, and the user is then presented with feedback, such as a corrective action, to aid the user in reducing the difference between the measured angle and the desired angle.

In one exemplary embodiment, a system for analyzing a position of a human body comprises an image capture device which captures an image of a human body; a user interaction unit where a user selects a position of the human body on the captured image; a comparison unit which determines an angle of the human body at the selected position and calculates a difference between an angle of the selected position and a desired angle of the selected position; and a display unit which displays feedback based on the calculated difference.

In another exemplary embodiment, a method for training a human body comprises capturing at least one image of a human body; selecting at least one position of the human body in the captured image; determining an angle of the human body at the selected at least one position; calculating a difference between the angle of the at least one selected position and a desired angle of the at least one selected position; and displaying feedback based on the calculated difference on a display.

These and other features, aspects, and embodiments are described below in the section entitled "Detailed Description."

BRIEF DESCRIPTION OF THE DRAWINGS

Features, aspects, and embodiments are described in conjunction with the attached drawings, in which:

FIG. 22 is a table displaying past and present technique, strength and performance readiness data for a list of users performing a bench press activity, in accordance with one embodiment of the invention;

FIG. 23 a table displaying an overall performance readiness rating for a list of users, in accordance with one embodiment of the invention;

FIG. 24 is an image of a message board user interface where a trainer can communicate with the user regarding specific techniques, performance readiness and corrective actions relating to the evaluation of the user's physical activity.

DETAILED DESCRIPTION

Figure 1:
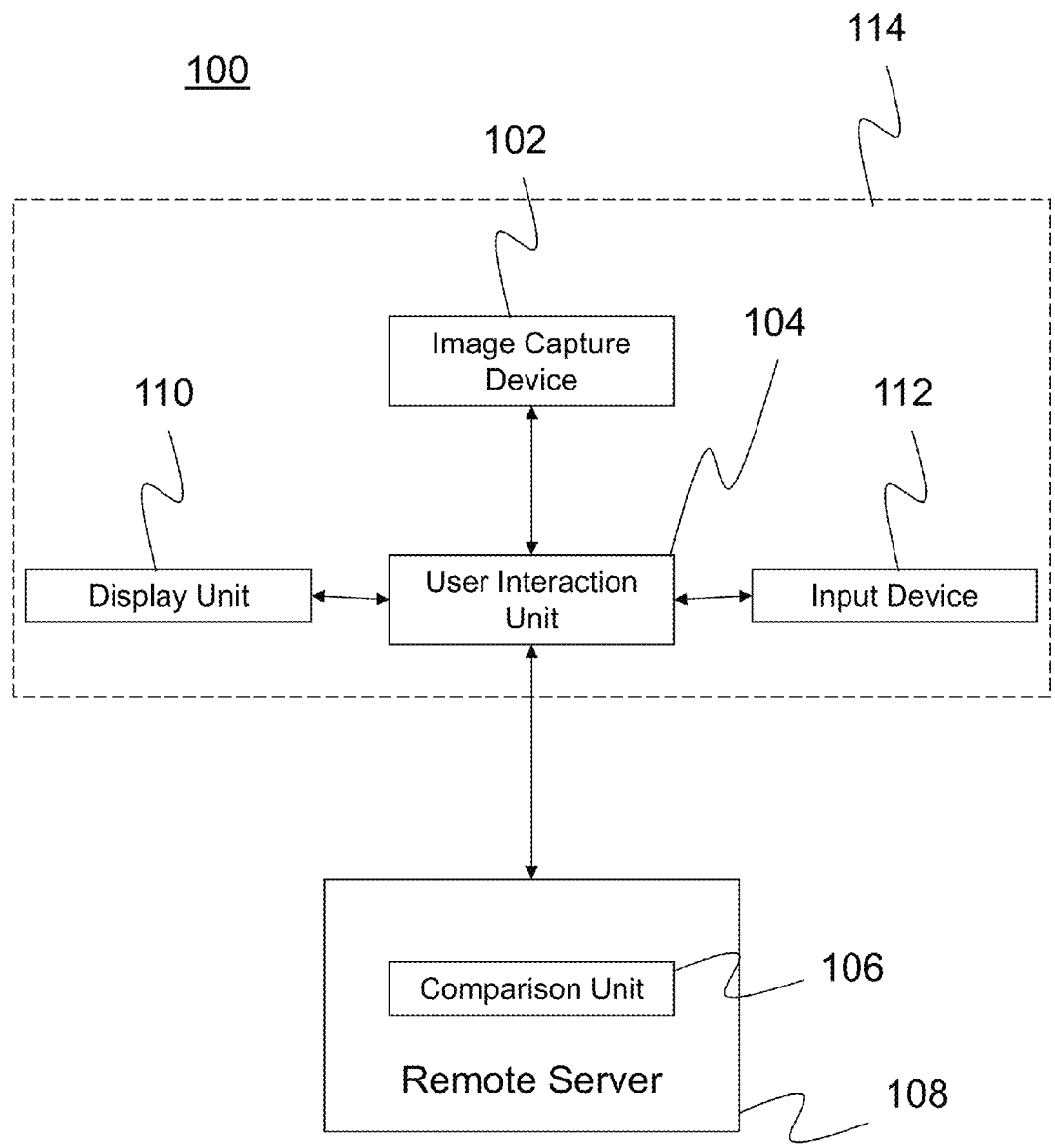
FIG. 1 is a block diagram of a system for analyzing position and movement in accordance with one embodiment.

In an athlete's training regimen, the ability to precisely measure, analyze and illustrate a body position of the athlete during specific movements is invaluable. Embodiments in accordance with the systems and methods described herein measure specific positions and movements of the human body, and provide data and visual information to system users (coach, trainer, athlete) to assist the athlete to make corrections in movement and body position. The system utilizes an image capture device such as a camera or video camera to measure movement and body position at a specific point in time without requiring the athlete to wear any sensors.

Systems and methods are also provided for evaluating and correcting physical performance of an activity by a human. A user performing one or more physical activities may be evaluated based on criteria relating to their movement, such as strength and technique. The user's performance in relation to these criteria is then rated, and the values for the criteria are combined to provide an overall performance score. The performance score is used to determine a user's overall readiness and ability to perform the physical activity which was evaluated or an overall ability to perform physical activities. Performance scores for more than one physical activity may be combined to provide an overall performance ready score that captures the person's overall physical ability. Comparisons of performance scores over time may provide information as to whether a user is improving or regressing, and could be specifically applied to evaluating physical rehabilitations from injuries or targeted types of training activities and techniques. Corrections to a user's technique can also be offered based on the specific rating the user received with regard to technique The system is a functional training tool. The purpose of a functional training tool is to improve performance. Therefore, all training that improves performance is by definition functional. Using specific functional training exercises will help an athlete's body focus on development of movement skills, body positions, and explosive power.

Movement mechanics are employed to teach an athlete how to improve athletic movement. Through web-based systems and methods disclosed herein, the flow of muscle reaction from the foot through the entire body, and the relationship of the upper body to the lower body, is measured. Such measurements allow an athlete to make corrections to existing movement mechanics to improve motion, strength, speed and athleticism. Through systems and methods disclosed herein, the strengths and weaknesses of the individual athlete may be evaluated and drills created to cue changes for each athlete and improve athletic performance.

It is important to recognize that physical development is not necessarily a point in time, but rather a continuum. One physical skill is related to, or dependent upon, another. The body is a system of muscles, tendons and ligaments that serve as connectors, stabilizers and prime movers causing action around the joint complexes. In order to move, certain muscles must create action, while others create reactive responses to allow motion. Being able to move parts of the body in the same plane, allows balance to occur as it moves. This requires training in first muscle response and reactive synchronized muscle action thereafter. Muscle stability and effective movement action is based on a series of rotations that occur around a joint, propelling direction of action.

The embodiments described herein use this basic understanding of the muscle/joint connection to develop functional strength and movement. Generally, earlier solutions focused on isolated muscle action; therefore, complete function was missing, and performance was compromised. In the embodiments described herein, the most basic of movement mechanics are used to develop the flow of muscle reaction that must occur from the foot through the entire body, creating efficient motion.

The first component to consider in movement mechanics is posture. If postural carriage of the body is compromised, so is the quality of the movement. Accordingly, it is necessary to train the upper body, hips and foot to be properly positioned throughout a movement or sequence of movements. This requires proper development of all relevant muscle groups, including the muscles of the lower leg, upper leg, and hips.

Timing is critical to this development process. The muscle system must contract, stabilize and create the necessary rotations to produce motion all in one action that maintains proper body position, readying the body for each successive action. These systems facilitate this development process.

Although the embodiments herein will be described with regard to athletic performance and activity, the systems and methods described herein may also be applied to analyzing and improving any type of movement by a human body, such a patient undergoing physical therapy to improve movement as a result of an injury or disease. For example, the system could be applied to a patient who has undergone knee surgery and needs to improve the movement of the knee. The system will then capture and analyze the patient's position and movement of the knee in order to determine whether the patient can move the knee as expected or whether the patient is making progress in increasing the movement of the knee.

Movement Training System

In accordance with one embodiment, a system for analyzing a position of a human body is provided, as illustrated in FIG. 1. The system 100 will include an image capture device 102, such as a still camera or video camera, which will capture the images or videos of the human body of an athlete or other subject. The image capture device 102 may be integrated into a portable electronic device such as a cellular phone, smart phone or tablet, and the portable electronic device may be capable of carrying out other aspects of the system, as will be described further herein. The image capture device 102 captures an image, video or sequence of images of an athlete performing some type of movement.

The captured image or video is then transmitted to a user interaction unit 104, such as a computer with a processor, memory and display, for processing and interaction with the user. In one embodiment, the images or videos are uploaded to a comparison unit 106 which may store the images or videos on a remote server 108 and provide calculations regarding the angles of the user's body in comparison with a desired angle. The images and the calculations may then be provided to a user over a web-based interface produced by the user interaction unit 104. The user interaction unit 104 provides a graphical user interface (GUI) (see FIG. 2) on an integrated or connected display unit 110 which displays the image or video so that the user can view and select a position on the human body. An input device 112 such as a mouse, keyboard, touch screen, voice recognition, etc. will allow the user to interact with the GUI. In one embodiment, the image capture device 102, the user interaction unit 104, the display unit 110 and the input device 112 may be integrated into a single portable device 114 such as a tablet, laptop or smart phone. By integrating all of the components of the system 100 into a single portable device 114, the system can be implemented in numerous environments, such as on a field, track, gym or other location where the athlete is training. The system is not limited to a closed environment where sensors and specialized equipment are required.

The GUI may provide the user with instructions on which position to select based on the type of activity that the athlete was engaged in. The GUI may also direct the user to select positions in a sequence of images so that the movement over the course of a time interval during which the images were taken may be determined, as will be described further below. In one embodiment, a position is selected by selecting two points on the human body which is then highlighted on the display with a straight line between the two points.

Once the user has selected one or more positions, the comparison unit 106 computes an angle of the position and compares the angle to a desired angle of that selected position. The angle may be relative to another part of the body or the ground surface, or even an object which the athlete is holding—such as a ball, bat, golf club, hockey stick, etc. The desired angle may be stored in a database within a memory of the comparison unit 106, with the values of various angles determined using known biomechanical measurements and parameters for a variety of activities. The comparison unit 106 then calculates a difference between an angle of the selected position and the desired angle of the selected position.

A display unit 110 may then display a corrective action to the user based on the calculated difference. The corrective action may be as simple as the calculated difference in the angles (i.e. −15 degrees), such that the athlete can understand the correction that is needed simply from the value of the difference. However, the corrective action may be more specific or practical, such as recommending that a runner further extend a foot or that a weightlifter further bend their knees. Regardless of the type of information provided, the corrective action is intended to help the athlete attain the desired angle of the selected position. If the display unit is a portable device such as a laptop, tablet or smart phone, the same portable device may be used to capture the image or video, select the positions and display the corrective actions. The integration of all of the primary operations of the system allows the system to be implemented in almost any training environment that the athlete may be using and will provide for the athlete to receive instant feedback regarding their movements.

Figure 2:
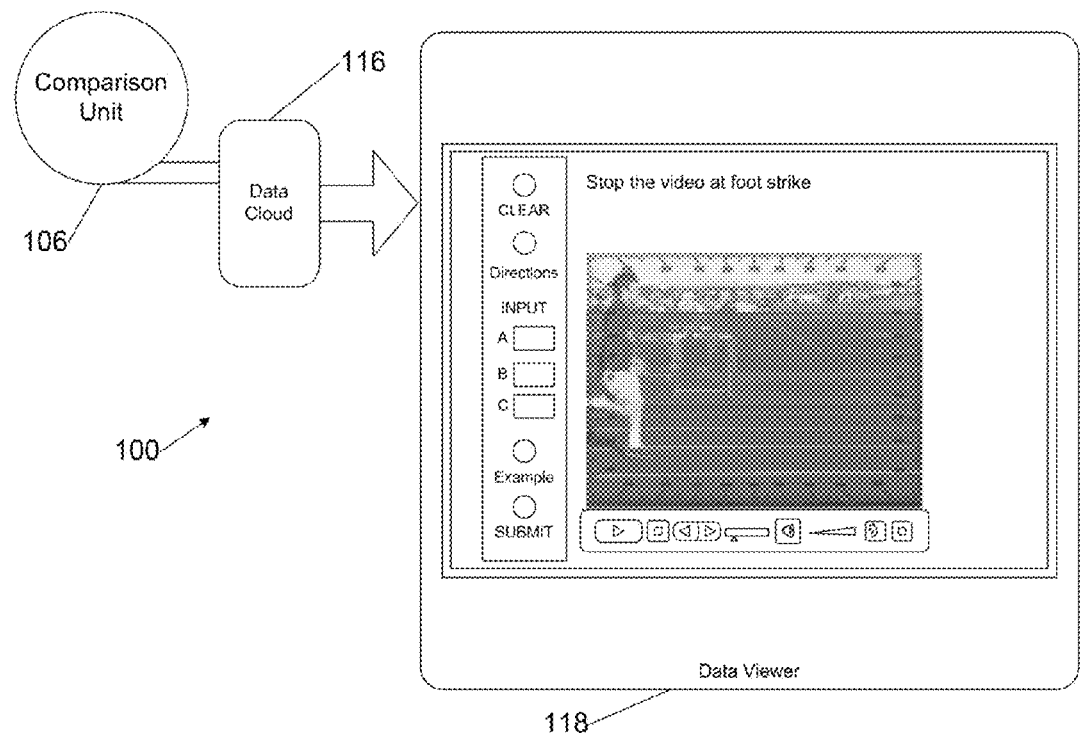
FIG. 2 is a block diagram of data flow in accordance with one embodiment.

Turning to FIG. 2, data flow for the system 100 in accordance with an embodiment is shown. The system 100 may include a database or data cloud 116 at the remote server 108 of possible outcomes for various exercises. For example, in one embodiment, the data can be generated using the comparison unit 106. The comparison unit 106 can include a computer simulation tool, previously run for a range of test cases (e.g., other athletes). In some embodiments, data cloud 116 uses input parameters and presents them directly to the comparison unit 106 for analysis. In such a situation, the analysis is for the particular athlete, using only the particular athlete's performance.

As used herein, a database includes succinct data information. In contrast, a data cloud includes succinct data information as well as tools to manipulate the data, e.g., algorithms, to derive secondary information, e.g., such as by interpolation. Both of these types of data storage, database or data cloud, can be referred to generally as a datastore.

The database or data cloud 116 can contain some or all possible combinations of corrections for various exercises of interest and individual athlete considerations. The data cloud 114 may be populated for a specific athlete, using athlete data such as information measured by the athlete in performing a specific exercise. The data cloud 116 may be populated by the athlete himself using a display 118 such as a monitor.

The display 118 is generated by the display unit 110 of the system 100 to set up the exercise technique or enter the measured exercise parameters. As used herein, the display 118 and display unit 110 may include the user interaction unit 104 as well as the hardware needed to implement the user interaction unit 104. The data associated with the selected exercise would then be used to extract the associated outcome in the data cloud 116.

Figure 18A:
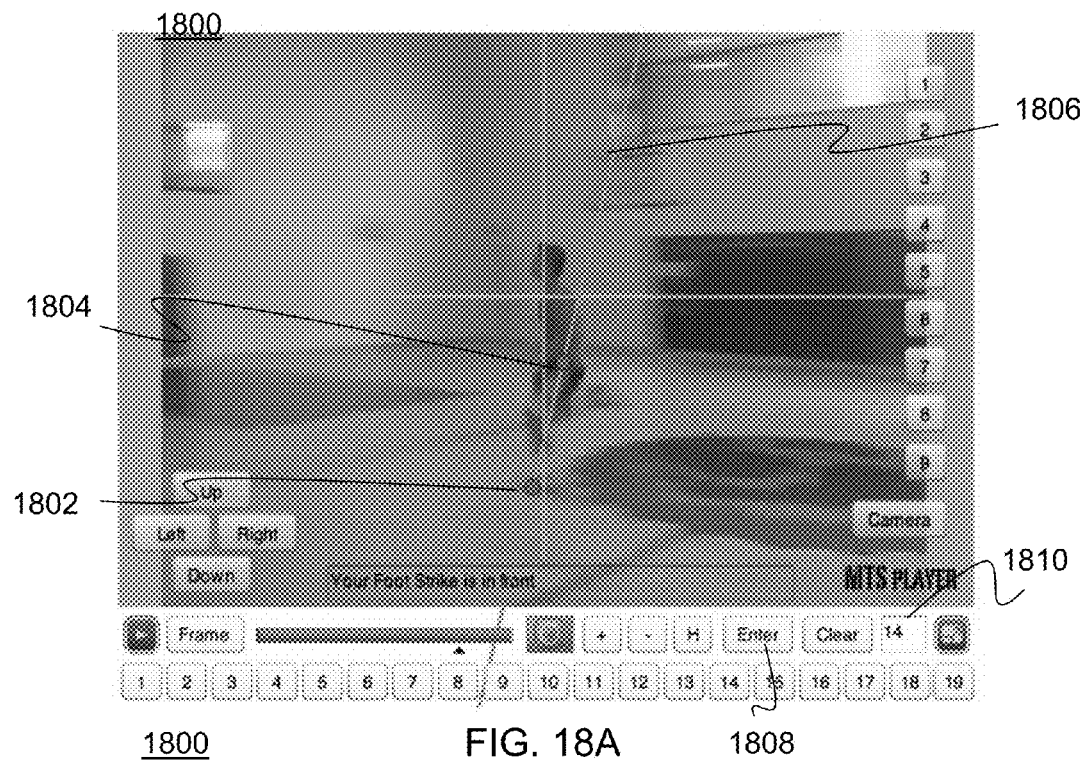
FIG. 18A is an exemplary screen shot illustrating a method of calculating the angle of a front foot as it strikes the ground in accordance with one embodiment.
Figure 18B:
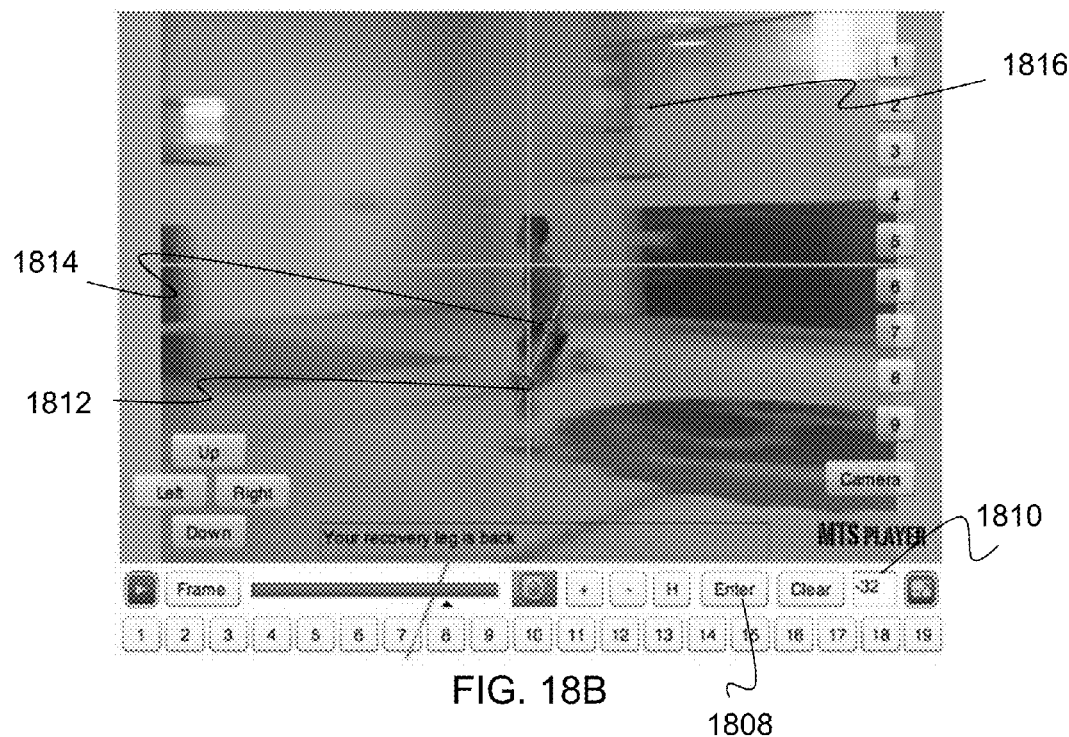
FIG. 18B is an exemplary screen shot illustrating a method of calculating the angle of a recovery leg in accordance with one embodiment.

It should be appreciated that in an alternate embodiment, the comparison unit 106 and/or data base or data cloud 116 can be located on the same portable device 114 as the display unit 110. Alternatively, the comparison unit 106 and/or data base or data cloud 116 can be located on a different computer system from the viewer system, as shown in FIG. 1 with the remote server 108. Exemplary embodiments of the computer systems which may be embodied by the image capture device 102, the user interaction unit 104, the comparison unit 106 or the portable device 114 as a whole are shown in FIGS. 18A and 18B.

The system allows the athlete to determine what adjustment should be made to his or her form, e.g., stance, positioning, etc., by interacting with the controls on the left panel with the display changing to indicate the required corrections to form based on information provided by the user.

One benefit of the embodiment is that the athlete is not required to wear any sensors or even perform the activity in a certain setting configured with sensors to measure movement or motion. A video or image of the athlete may be taken in any setting, such as during a team practice, at a gym, etc., and the video can be immediately uploaded from the portable device 114 to the remote server 108 which processes the video and provides the GUI for the user to select positions. This process is designed to take only a few seconds or minutes, depending on whether the video is uploaded from the image capture device 102 or is first transferred to another computer (not shown) which is connected to the remote server 108 through a network. The analysis can then be immediately displayed to the user on the display 118. The user is therefore able to obtain near real-time feedback on the athlete's movement and provide that feedback to the athlete during a training session or practice, so that the athlete can make immediate corrections. The system can significantly improve the benefits of a practice or training session and reduce the amount of time needed for an athlete to improve movement mechanics and athletic performance.

In accordance with one embodiment, the initial level of an athlete's ability is measured, e.g., by measuring the athlete's performance in completing an athletic task. Recommendations are then made to the user or athlete on how to improve performance. The athlete's performance is then measured again in order to determine the improvement the athlete achieved. The performance of the athlete may be measured through the angles of movement, strength measurements, speed measurements and even lean muscle mass measurements.

The data being collected during the training sessions and the use of the system is also valuable for other reasons. In one embodiment, the data on how quickly an athlete improves over the course of numerous training sessions can be used to model a predicted course of improvement for an athlete over a period of time. For example, if data from other athletes is modeled, the system can provide expected goals for a future athlete to attain at certain steps in the process based on the previous improvements of other athletes utilizing the system. This analytical application will help a user (such as a coach, trainer or the athlete) determine whether the athlete is improving his or her movement along a normal pace, a slower pace or a faster pace. A coach may be able to determine whether an athlete has been completing a recommended schedule of training or whether an athlete may be more skilled than others, and adjustments can then be made to the training regimen.

In addition to training an athlete, in one embodiment, the data collected from the use of the system may be compiled to also assess the effectiveness of a particular type of training activity. In other words, the degree of improvement of the athletes in response to different types of training programs may be analyzed to determine if one training program is more effective than another in improving the athletes' movement and performance.

Training Foot Movement

In one embodiment, the system may analyze and assess movement of a foot. Creating proprioceptive activity to the necessary muscles to initiate motion is a primary component to the timing of muscle reaction. If the foot does not function correctly, neither will movement. Therefore, many types of movement essentially begin in the foot. Based on this premise, it is evident that training the muscular use of the foot is critical. Using thermographic photos of functional reaction on the soles of the feet during gait, drills can then be established that train a functional muscle response in the feet. Due to years of compensation, many athletes fall inside on the feet, walk on the outsides of the feet, or lean back or forward due to a lack of stability on the mid foot. These systems and methods use the drills to teach the correct mechanical function and strengthen the muscles of the foot, to begin movement training. Observation of athletes has made it apparent that very few of them produce motion from their feet, but, rather, leaned forward and basically "fall" into a direction of movement. This creates an off-balance position, and results in a slower than desired rate of movement (first step speed).

Based on these basic principles of movement, the present systems and methods facilitate improvement in an athlete's functional strength, which is necessary to produce the power, balanced speed and quickness required for optimal performance. However, just being able to move a lot of weight in the gym will not necessarily transfer to use of that strength on the field or court.

An exemplary scenario guiding an athlete using the system 100 will now be described. Unless specified otherwise, FIGS. 3-14 illustrate actions performed by the viewer system. Also, references to anatomy are intended to be references to representations in the system 100 (e.g., underlying data).

Figure 3:
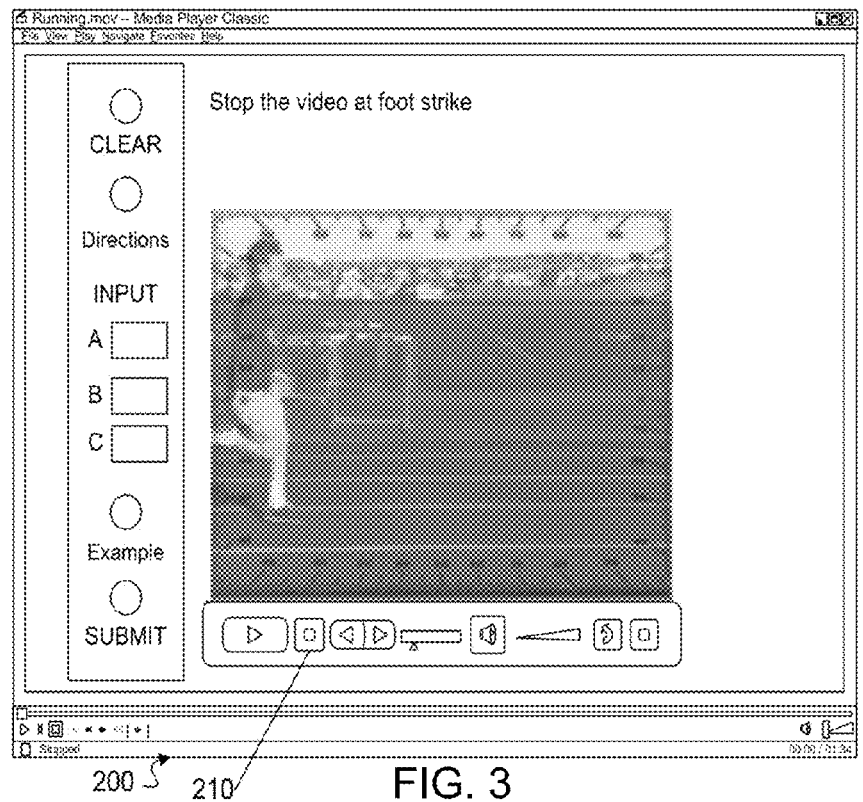
FIG. 3 is an exemplary screen shot illustrating a first sprinting position in accordance with one embodiment.

Turning not to FIG. 3, in a first step, the athlete or user launches the software application for movement training, also referred to interchangeably as movement training application described in further detail in FIGS. 18A and 18B. In some embodiments, the movement training application of the comparison unit produces the GUI see on the display 118. Thus, the movement training application receives data from database 116, which may be produced by the comparison unit 106. The movement training application may be launched from a desktop icon, and run locally from the portable device 114, the user's computer, tablet, smart phone, or other electronic device. Alternatively, the movement training application may be accessed via the internet, and run on the remote server 108.

Upon launching the movement training application, the display or screen 118 displays a preloaded case representing a model athlete. Alternatively, data on a specific athlete could be loaded at this point. This specific athlete data may be loaded by the user or athlete by selecting, e.g., a previously recorded video of the athlete. The athlete data, regardless of source is the starting point for the rest of the movement training analysis. This athlete data, combined with measured parameters obtained from the data, determines the outputs displayed.

Still referring to FIG. 3, in a first step, the user plays a previously recorded video or sequence of images of an athlete performing a predetermined exercise. For example, FIGS. 3-14 all relate to an athlete participating in a 40-yard sprint. During the course of playing the video, the movement training application presents the user with various instructions which ensure that the user makes certain measurements at predesignated times. For example, in FIG. 3, the user is instructed to "Stop the video at foot strike." Thus, the user should click on the stop button 210 once the athlete's foot touches the ground in the video.

Figure 4:
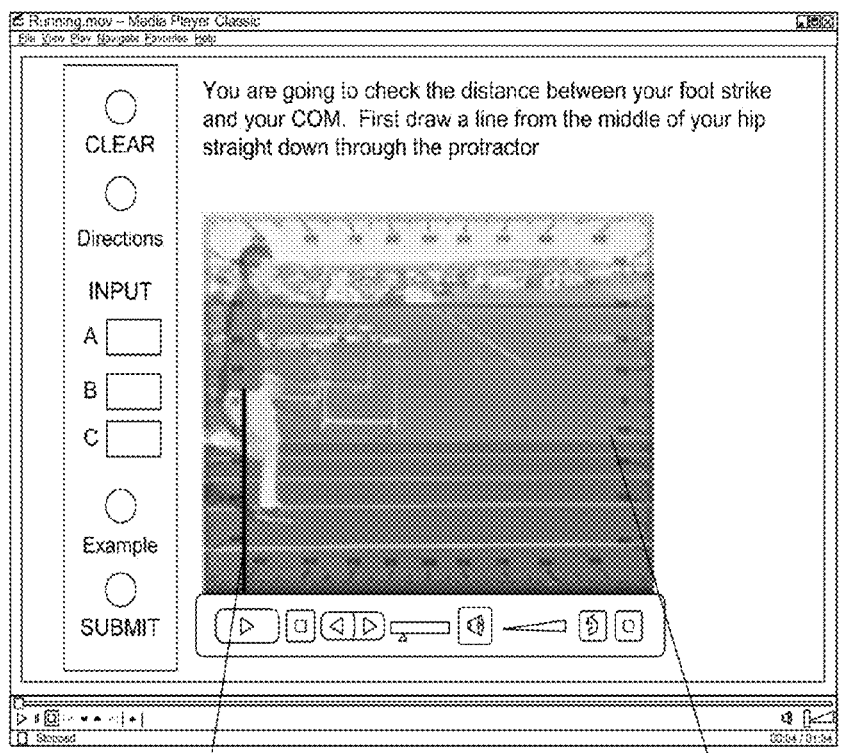
FIG. 4 is an exemplary screen shot illustrating a first sprinting position in accordance with one embodiment.

Referring now to FIG. 4, in a second step, the user is informed that he is going to check the distance between the foot strike and the athlete's center of mass ("COM"). In order to do this, a message is displayed on the screen 118 which instructs the user to "First draw a line from the middle of your hip straight down through the protractor." In one embodiment, the user is able to draw a line on the screen with an input device 112, such as by clicking a mouse on a spot where the line should begin and dragging the mouse to a spot where the line should end. A protractor may, in some embodiments, be built into the screen as a border 310 for the video to aid in identifying the line that should be drawn. This line from the hip is illustrated as numeral 320.

Figure 5:
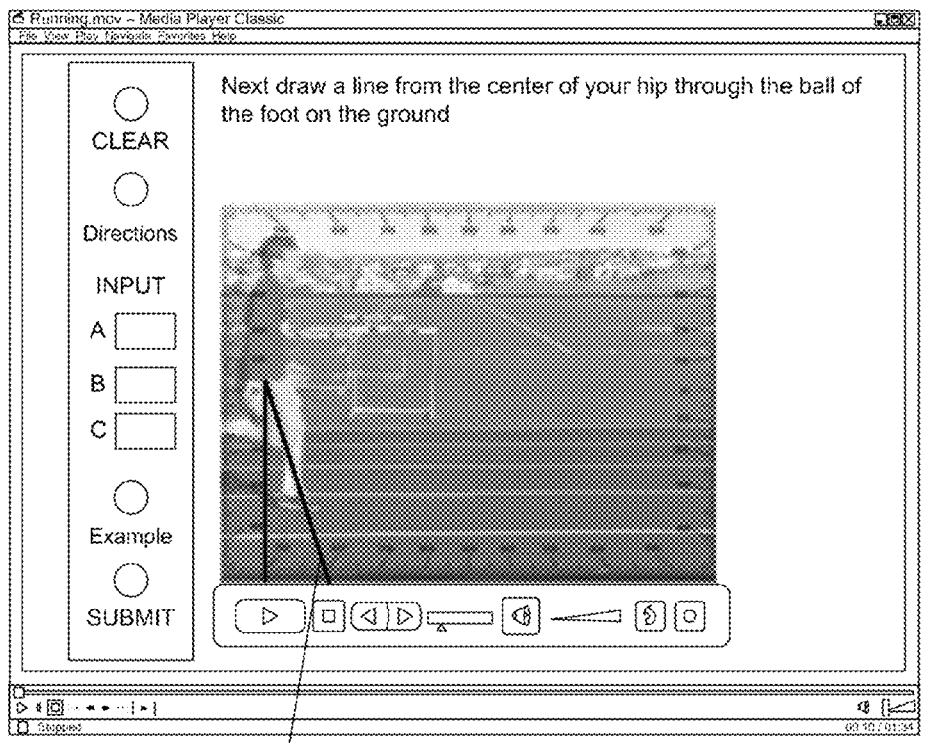
FIG. 5 is an exemplary screen shot illustrating a first sprinting position in accordance with one embodiment.

Referring now to FIG. 5, in a third step, the user is instructed to "Next draw a line from the center of your hip through the ball of the foot on the ground." This line from the hip through the foot is illustrated as numeral 410.

Figure 6:
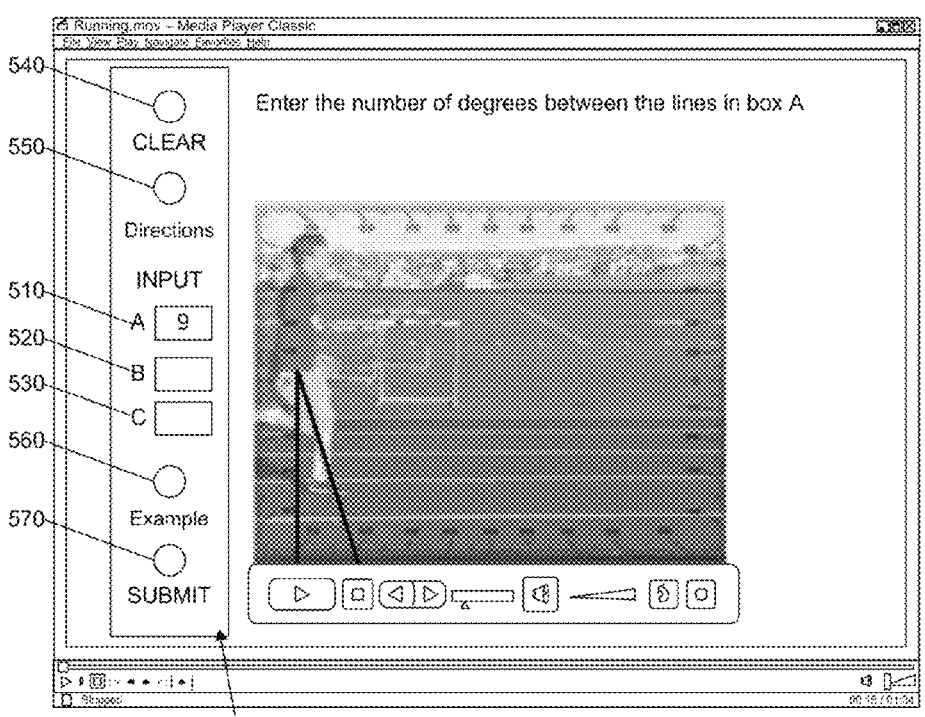
FIG. 6 is an exemplary screen shot illustrating a first sprinting position in accordance with one embodiment.

Referring now to FIG. 6, in a fourth step, the user is informed that he is going to measure the difference in degrees between the two lines he has drawn 320, 410. Thus, a message is displayed on the screen 118 to instruct the user to "Enter the number of degrees between the lines in box A." Box A is a first input field and is represented by numeral 510. In one embodiment, the movement training software may be programmed to determine the slope of the lines and convert them to degrees, which can then be subtracted to determine the difference between the angle of the athlete's body part and that of the desired angle.

Box A is one of the controls on the left panel 505, for which the user interacts with to determine how to improve the athlete's performance. Also included in left panel 505 are Box B 520 and Box C 530, which are also input fields, and the following buttons: Clear 540, Directions 550, Example 560 and Submit 570. Clear button 540 clears the input values in boxes 510, 520 and 530. Directions button 550 provides user interface directions allowing the user to input personal performance data onto a film clip of the user running or performing prescribed lifts (e.g., instructs user on how/where to draw lines and compute protractor degrees to insert into data input spaces on page). Example button 560 provides visual examples of proper or optimal technique with respect to running or the prescribed lifts. In some embodiments, example button 560 is replaced by a corrections button (e.g., on the user account version), similarly providing visual examples of proper or optimal technique. Submit button 570 submits the entered values from Boxes A-C, 510-530.

Referring still to FIG. 6, the user is able to determine the difference between lines 320, 410 by looking at the angle measurements on the protractor and subtracting one from the other and entering the absolute value of the difference in Box A 510. As shown in FIG. 5, the difference in degrees between lines 320 and 410 is 9. In one embodiment, the measurement automatically appears on the screen when the user finishes drawing the second line. As previously described, the movement training software may be programmed to determine the slope of the lines and convert them to degrees, which can then be subtracted to determine the difference between the angle of the athlete's body part and that of the desired angle.

Figure 7:
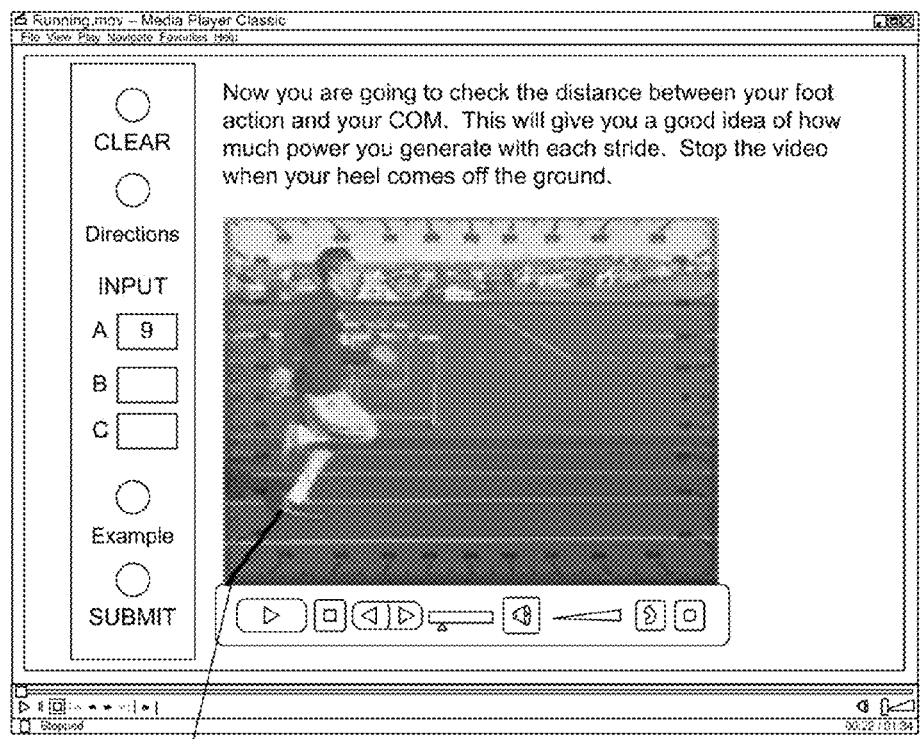
FIG. 7 is an exemplary screen shot illustrating a second sprinting position in accordance with one embodiment.

Referring now to FIG. 7, the user is informed that he is going to check the distance between the athlete's foot and COM. This is intended to give the user a good idea of how much power the athlete is generating with each stride. In a fifth step, the user is instructed "Stop the video when your heel comes off the ground." The rear heel of the athlete is identified by line 610.

Figure 8:
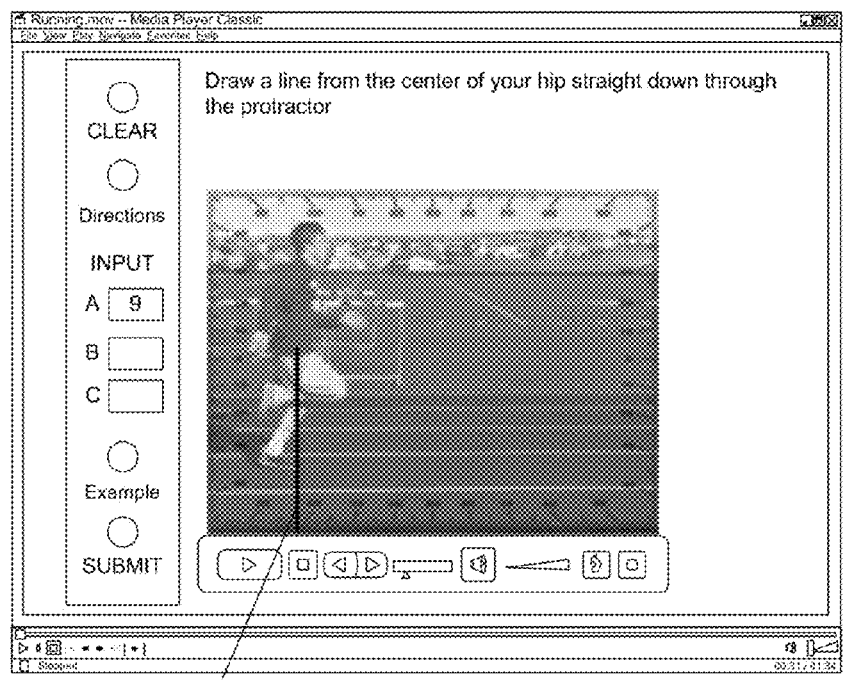
FIG. 8 is an exemplary screen shot illustrating a second sprinting position in accordance with one embodiment.

Referring now to FIG. 8, in a sixth step, the user is instructed to "Draw a line from the center of your hip straight down through the protractor." This is similar to the task done in FIG. 4. This line from the hip is illustrated as numeral 720.

Figure 9:
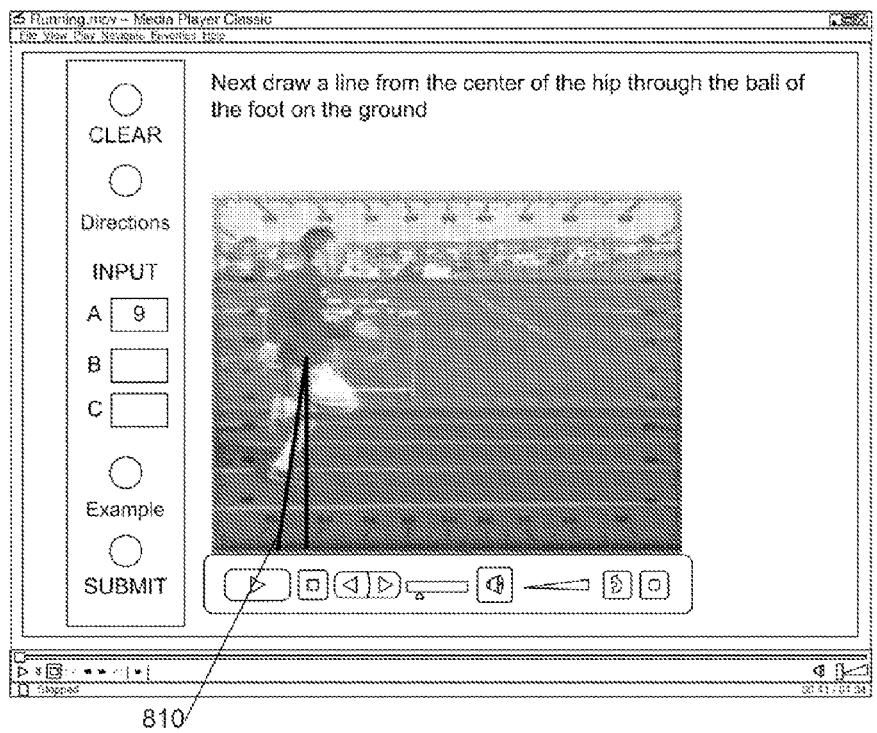
FIG. 9 is an exemplary screen shot illustrating a second sprinting position in accordance with one embodiment.

Referring now to FIG. 9, in a seventh step, the user in instructed to "Next draw a line from the center of the hip through the ball of the foot on the ground." This is similar to the task done in FIG. 5. This line from the hip through the foot is illustrated as numeral 810.

Figure 10:
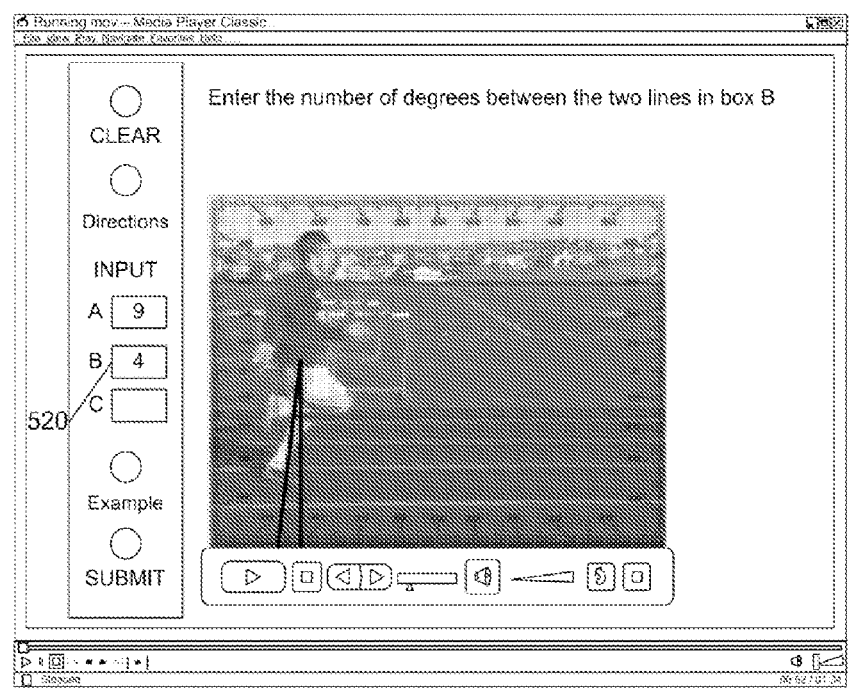
FIG. 10 is an exemplary screen shot illustrating a second sprinting position in accordance with one embodiment.

Referring now to FIG. 10, in an eighth step, the user is informed that he is going to measure the difference in degrees between the two lines he has drawn 720, 810. Thus, the user is instructed "Enter the number of degrees between the two lines in box B." The user is able to determine the difference between lines 720, 810 by looking at the angle measurements on the protractor and subtracting one from the other and entering the absolute value of the difference in Box B 520. As shown in FIG. 10, the difference in degrees between lines 720, 810 was 4. In one embodiment, the measurement automatically appears on the screen when the user finishes drawing the second line.

Figure 11:
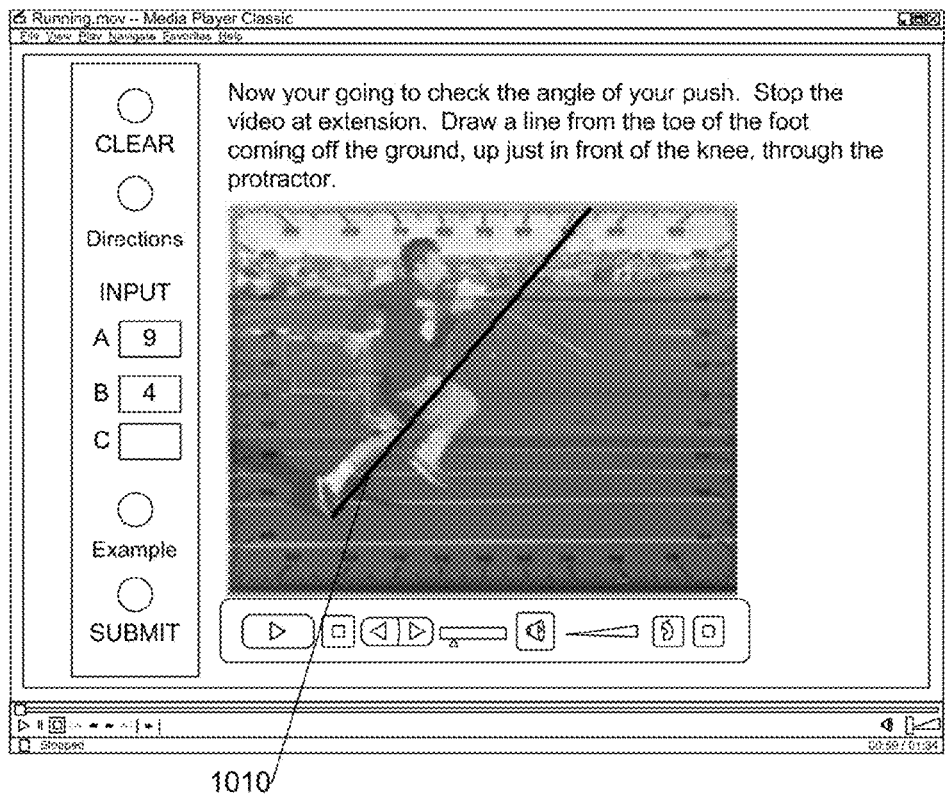
FIG. 11 is an exemplary screen shot illustrating a third sprinting position in accordance with one embodiment.

Referring now to FIG. 11, in a ninth step, the user is informed that he is going to check the angle of the athlete's push. The user is instructed to "Stop the video at extension. Draw a line from the toe of the foot coming off the ground, up just in front of the knee, through the protractor." This line from the toe is illustrated as numeral 1010.

Figure 12:
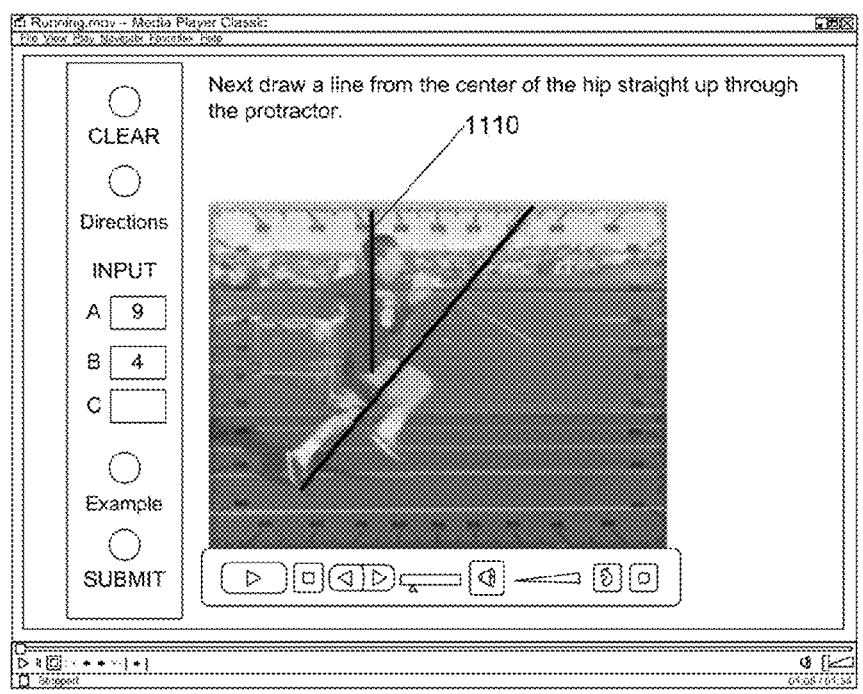
FIG. 12 is an exemplary screen shot illustrating a third sprinting position in accordance with one embodiment.

Referring now to FIG. 12, in a tenth step, the user is instructed to "Next draw a line from the center of the hip straight up through the protractor." This line from the hip is illustrated as numeral 1110.

Figure 13:
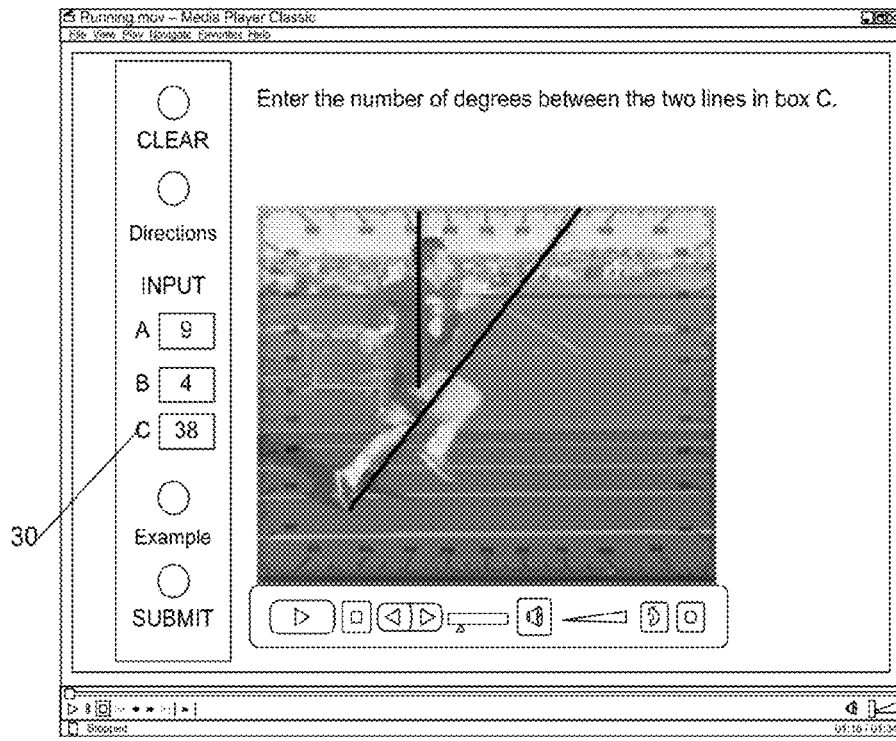
FIG. 13 is an exemplary screen shot illustrating a third sprinting position in accordance with one embodiment.

Referring now to FIG. 13, in an eleventh step, the user is instructed to "Enter the number of degrees between the two lines in box C." The user is able to determine the difference between lines 1010, 1110 by looking at the angle measurements on the protractor and subtracting one from the other and entering the absolute value of the difference in Box C 530. As shown in FIG. 13, the difference in degrees between lines 1010, 1110 was 38. In one embodiment, the measurement automatically appears on the screen when the user finishes drawing the second line.

Figure 14:
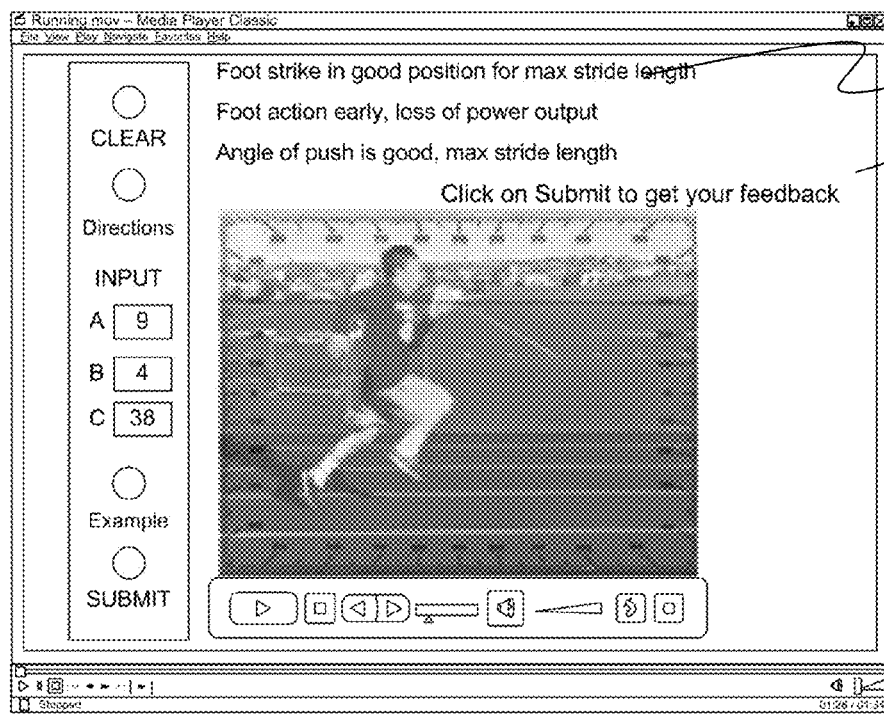
FIG. 14 is an exemplary screen shot illustrating a third sprinting position in accordance with one embodiment.

Referring now to FIG. 14, the user is instructed at box 1402 to "Click on Submit to get your feedback." Thereafter, the movement training application provides the user with information in a feedback area 1404 related to measurements made by the user in FIGS. 3-13. For example, in FIGS. 3-6, foot strike was examined, in FIGS. 7-10, foot action was examined, and in FIGS. 11-13, angle of push was examined. Thus, the information provided to the user in this example relates to these three items. As shown in FIG. 14, the output provided to the user in the feedback area 1404 is as follows: "Foot strike in good position for max stride length; Foot action early, loss of power output; Angle of push is good, max stride length." While shown in the same screen as the instructions, the output of the movement training application may be provided in a separate screen. In some embodiments, output includes information (e.g., actions/drills) required for or desirable for making corrections.

User Feedback

In some embodiments, the user or athlete will be able to click on the various outputs or conclusions supplied by the movement training application and get a more detailed analysis. For example, in some embodiments, the performance of each of the items examined may be rated on scale (e.g., such a 1 to 100), the user or athlete can monitor and aim to improve. Thus, using the movement training application can be an iterative process, where the athlete continues to monitor his performance and take measurements to ensure that his performance is improving.

In some embodiments, when the user hits submit, comparison unit can examine the data in Boxes A-C. 510-530, and provide a score, e.g., between 1-100, or a letter grade score, e.g. "A," "B," etc. The user can also be provided feedback to help them improve their scores. In one embodiment described further below, the user may be told "Your upper body is too high" so that the user receives advice on how to correct the degrees at which their movement or position departs from the desired angle. In other embodiments, exercises, drills, movements, etc., can be suggested based on the user's score and the analysis performed.

While the present example has described a single user or athlete's review of the athlete's performance, the movement training application allows each athlete to have an individual account which may be accessed through the main website. For example, each athlete's performance of lift, run, drill, etc., is accessible on his or her account. The athletes are able to draw lines, by way of direction, to show body position throughout and allow interactive learning of correct positioning.

Figure 15:
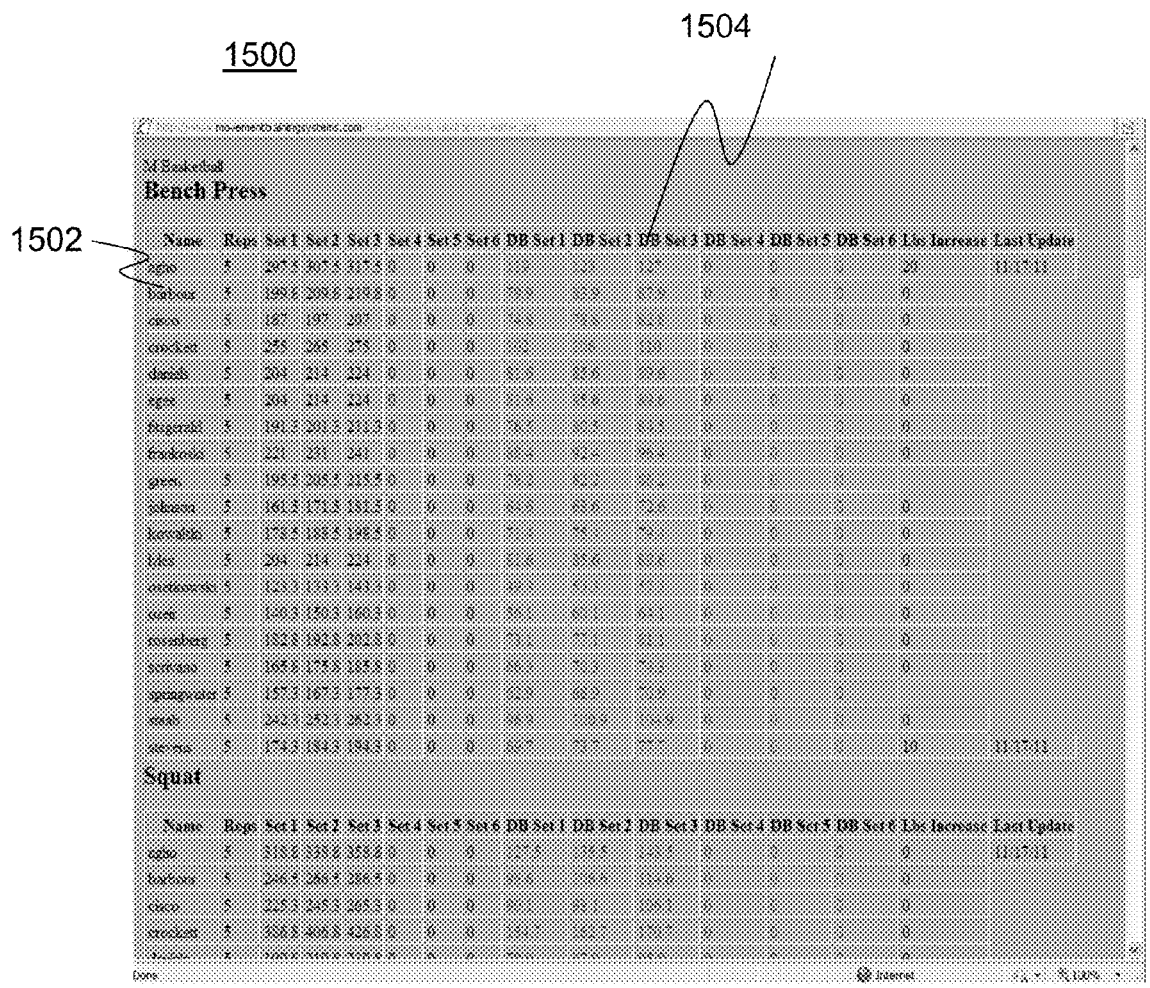
FIG. 15 is an exemplary screen shot of a comparison table for comparing the measurements of multiple athletes over the course of several training sessions, in accordance with one embodiment.

In another embodiment illustrated in FIG. 15, the data for multiple athletes can be compiled and presented in a table 1500 to evaluate an athlete's progress over the course of a training program and compare the athlete to other athletes participating in the same program. Individual athletes can be listed by name (or a designated generic identifier) on the multiple rows 1502, and the data compiled during their training sessions can be displayed in the multiple columns 1504 across the top of the table 1500. In one embodiment, the data may include the difference in calculated angles over the course of several training sessions so that the user or athlete can determine if their movement and positions are improving. In another embodiment, the user or athlete may be prompted to enter additional information into the GUI which will provide further analysis of the progress of the athlete through the training programs. For example, the amount of weight that an athlete lifts in a bench press may be input and displayed over the course of several training sessions to show whether an athlete is increasing the amount of weight being lifted as they go through the movement training process. The effectiveness of the movement training system can then be evaluated in terms of the athlete's improved performance, strength, speed or any other quantitative category which can be measured and entered into the system.

Training Lifting Movements

Figure 16A:
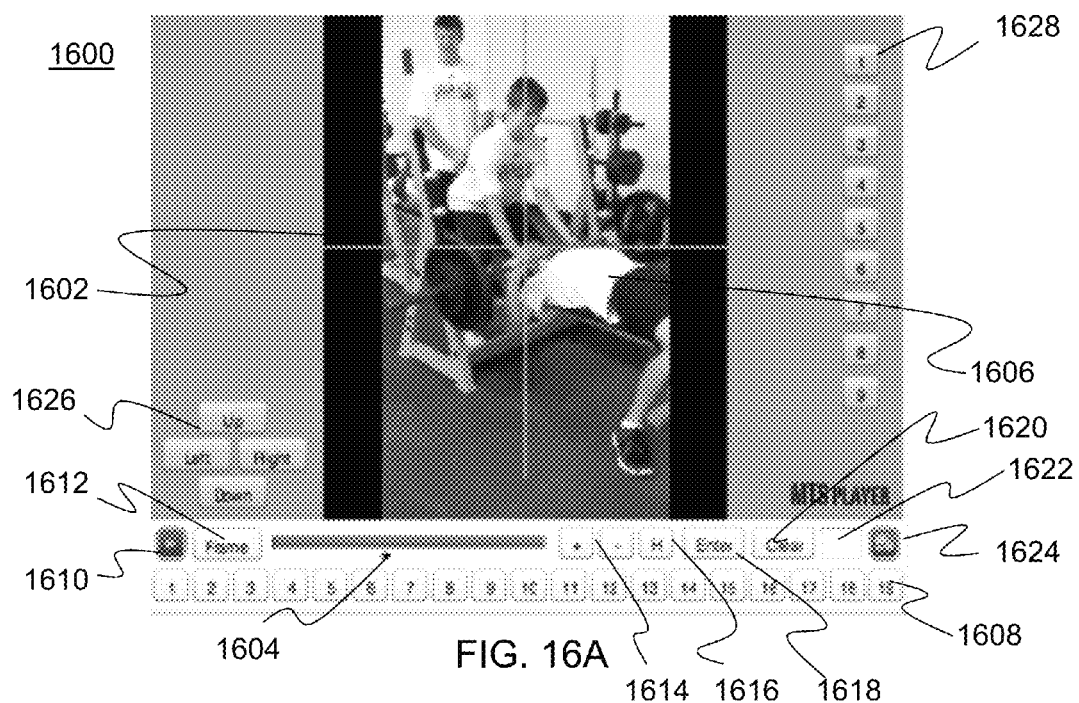
FIGS. 16A-16D illustrate the steps of calculating an angle of a forearm during a bench press in accordance with one embodiment.

In one embodiment, an athlete may be trained in a weight-lifting activity such as a bench press, as illustrated in FIGS. 16A-16D and 17A-17C. The user opens the movement training application on the portable device and sees the GUI 1600 shown in FIG. 16A. FIG. 16A illustrates a screen shot of the GUI 1600 where the user is asked to stop the video 1602 at a specific time 1604 in the video sequence when the athlete 1606 in the video is at a specific position in the bench press movement. At the bottom of the GUI are video buttons 1608 labeled "1-19," which allow a user to view up to nineteen different videos per activity. Selecting button "1" will play a first video sequence of the athlete completing a single bench press action.

The remaining sections of the GUI 1600 will be explained below. A start/stop button 1610 allows the user to start and stop the video, and a Frame-by-Frame button 1612 allows the user move through the video sequence frame-by-frame, as shown by the time marker 1604. Zoom buttons 1614 allow the user to zoom in or out on the image to better identify the athlete's position. A home page button 1616 (H) allows the user to return to the main GUI of the application, and an Enter button 1618 allows the user to tell the application to calculate the difference in angles once the user has selected appropriate positions on the athlete's body 1606. A Clear button 1620 resets the entire method, and a degree of correction box 1622 displays the difference between the desired angle and the measured angle. A full screen button 1624 expands the GUI to fill an entire screen of a display for easier viewing. Navigational buttons 1626 "up, down, left, and right" are used to move the video 1602 around the GUI 1600. Sequence buttons 1628 labeled 1-9 on the right side refer to different types of measurements that can be made for any one activity (such as the bench press). There may be more or less measurements depending on the type of activity, to the number of sequence buttons 1628 is not limited to only 9. Although not illustrated here, the GUI may also include a message button which may be used to send messages to the athlete in the video or other users to discuss the measurements being observed or tips on correcting certain movements.

Once the video is loaded, the user will select one of the sequence buttons 1628 on the right side of the GUI. These are the buttons used by the user to evaluate a specific type of movement during the activity. In this embodiment, there are two different sequences for the bench press activity. Sequence 1 is a forearm position, and Sequence 2 is the upper arm position.

Figure 16B:
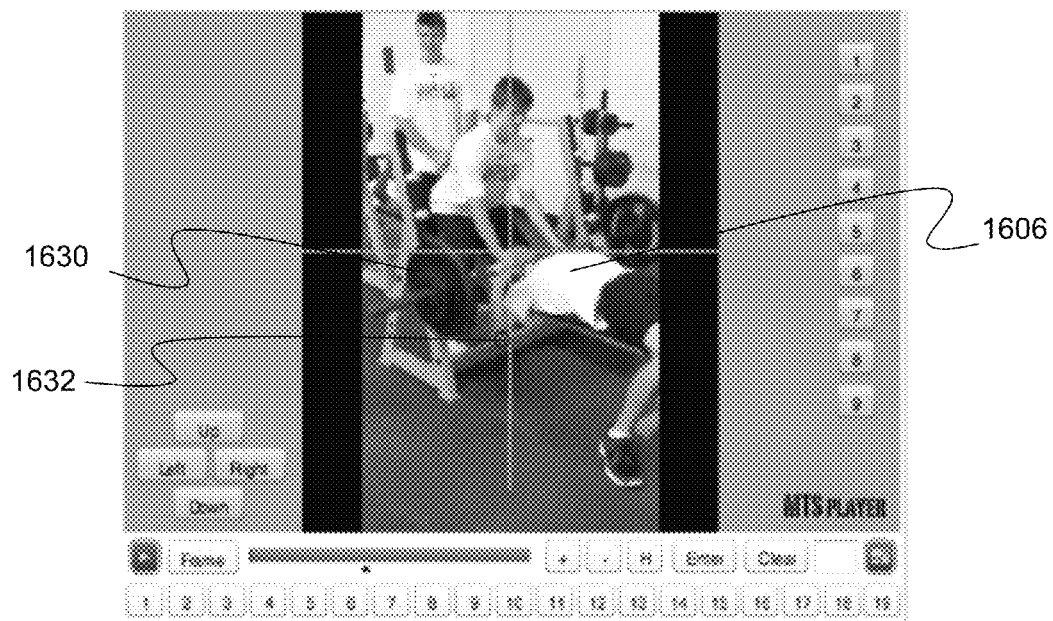
Figure 16C:
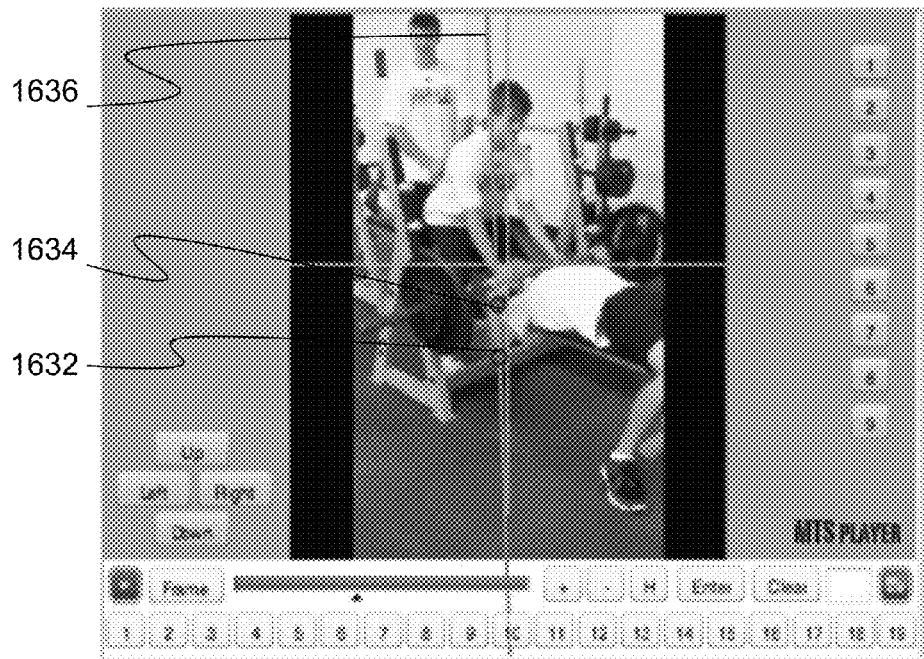
Figure 16D:
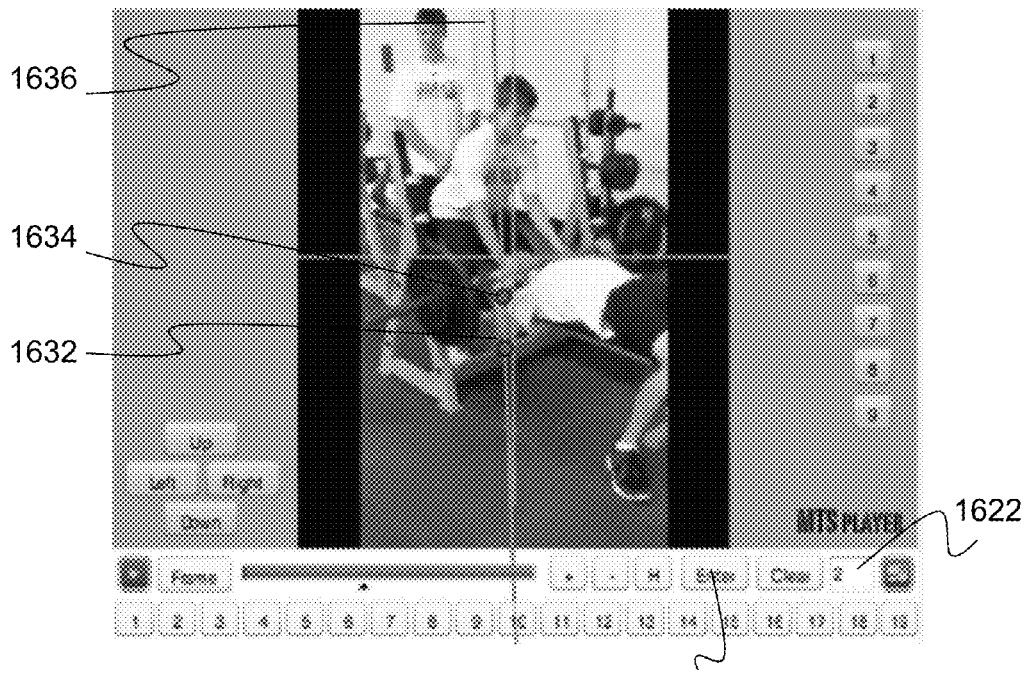

To evaluate Sequence 1 (forearm position), the video is advanced frame-by-frame to the frame where the weight 1630 is at its lowest position (resting on the chest of the athlete 1606), as shown in FIG. 16B. The user is then prompted to identify the middle of the elbow and select a first point (by clicking the mouse at that point), and a first dot 1632 is created on the user-selected point. The user is then prompted to select a second point on the middle of the wrist, and a second dot 1634 is created at that point, as shown in FIG. 16C. A straight line 1636 appears which passes through the middle of the first dot 1632 and second dot 1634. As shown in FIG. 16D, once the user selects the "Enter" button 1618, the movement training application measures the angle between the two dots

1632, 1634. This is the angle of the user's forearm. By clicking on the "Enter" button 1618, the application compares this angle with a desired angle stored in a database, and outputs a degree of correction in the correction box 1622. In this embodiment, the degree of correction is "2," which may indicate to the user that the athlete needs to adjust the position of the forearm by 2 degrees. If the number was negative (i.e. −2), this would tell the user that the athlete needs to adjust the position of the forearm by 2 degrees in the opposite direction. The basic process of movement training is now complete.

Figure 17A:
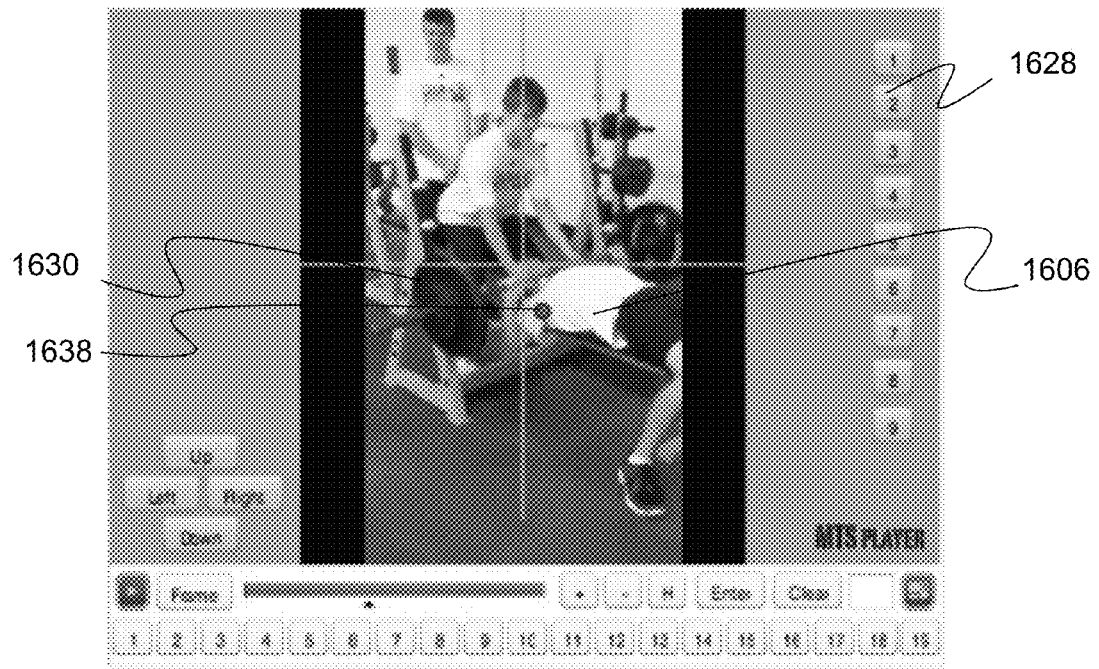
FIGS. 17A-17C illustrate the steps of calculating an angle of an upper arm during the bench press in accordance with one embodiment.
Figure 17B:
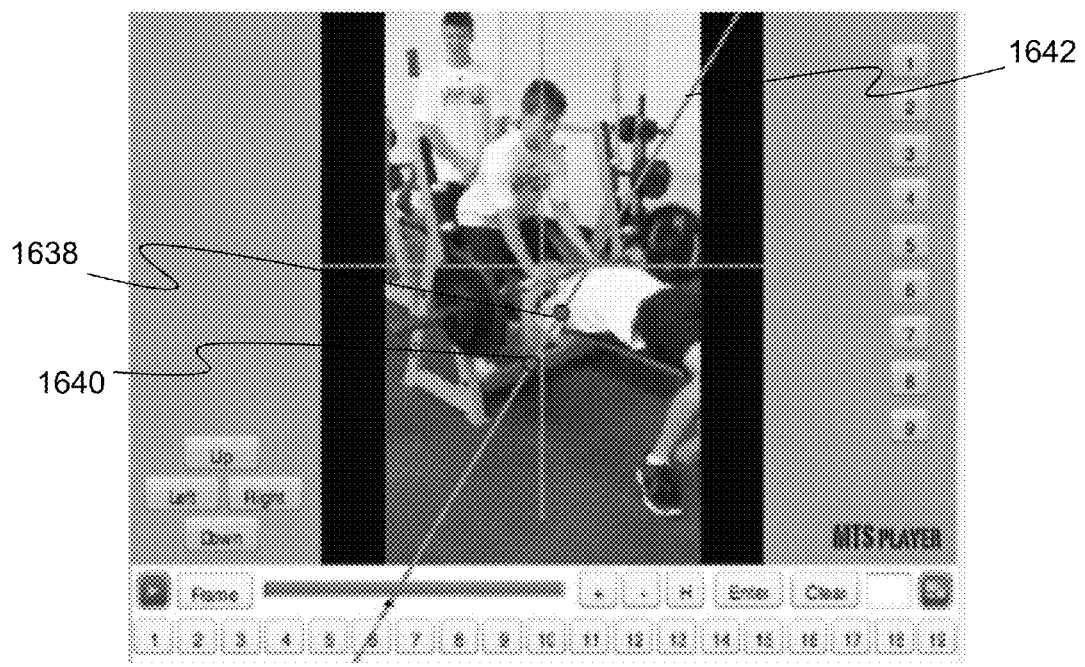
Figure 17C:
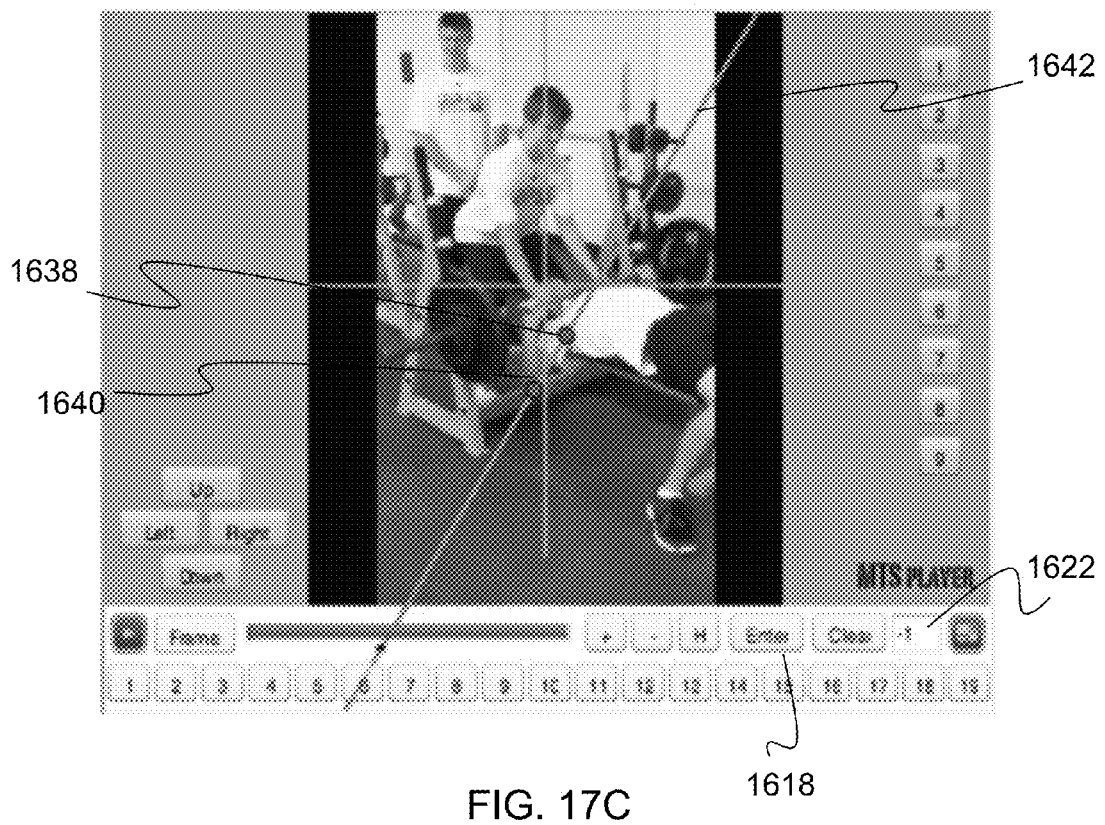

To complete a second movement training operation for a different type of movement, the user can select the "Clear" button 1620 which removes the dots, lines and degree of correction, as illustrated in FIG. 17A. The user may now click on Sequence 2 from the sequence buttons 1628 in order to now calculate the position of the upper arm during the bench press. The video is advanced to the same time as previous, where the athlete 1606 has the weight 1630 at a lowest position. The user is prompted to select a point at the middle of the armpit, and a first dot 1638 appears. In FIG. 17B, the user is asked to click on a point at the middle of the elbow, and a second dot 1640 appears, followed by a straight line 1642 which passes through the middle of the first dot 1638 and second dot 1640. This is the angle of the user's upper arm. As shown in FIG. 17C, by clicking on the "Enter" button 1618, the application compares this angle with a desired angle stored in a database, and outputs a degree of correction in the correction box 1622. In this embodiment, the degree of correction is "−1," which may indicate to the user that the athlete needs to adjust the position of the forearm by 1 degree. If the number was positive (i.e. 1, this would tell the user that the athlete needs to adjust the position of the forearm by 1 degree in the opposite direction. The basic process of movement training is now complete.

It should also be appreciated that while the calculation of the angles in Sequence 1 and Sequence 2 were done separately, these calculations may be completed in a single combined sequence where the user measures the position of the forearm and the position of the upper arm at the same time. Both angles of correction may be displayed simultaneously and could therefore be used to understand the relationships of the position of one part of the body to another. For example, the angle of the upper arm may influence the angle of the lower arm, and so correcting the angle of the upper arm will automatically improve the angle of the forearm. The system can illustrate this to the user and the athlete to better improve the athlete's movement.

In another embodiment, the user may want to compare videos from different sessions by selecting different video buttons 1608 along the bottom of the GUI. The user can then compare an athlete's movement and position over a period of time through several training sessions in order to determine if the athlete is improving, staying the same or regressing.

The system and method described above with regard to the lift training may also be applied to the foot training, as shown in FIGS. 18A and 18B. FIG. 18A illustrates a GUI 1800 showing a method of calculating the angle of a front foot as it strikes the ground. As previously described with respect to the bench press movement, a first dot 1802 is placed where the front foot hits the ground, and a second dot 1804 is placed at the athlete's hip area. The line 1806 is then drawn between the first dot 1802 and second dot 1804, and the user selects "Enter" 1808 to have the difference between the athlete's angle and a desired angle be output in the correction box 1810. FIG. 18B illustrates the method of identifying the angle of the back leg, or recovery leg, during a running motion. A first dot 1812 is placed at the knee of the recovery leg, and a second dot 1814 is placed at the hip of the athlete. The line 1816 is drawn between the two dots, and the user hits the "Enter" button 1808 to receive the difference between the athlete's measured angle and the desired angle output to the correction box 1810.

The info that the coach and the athlete obtained from this evaluation will enable the athlete to make a correction before it results in an injury or poor performance on the field. Exercise or skill, done out of position, effects performance in a negative way. All activities are evaluated the same way (body position in motion).

Training Rotational Movement

Rotational components are critical to efficient movement; they are the body's mechanism to produce motion. The strength an athlete attains must be that which produces rotational stability along with prime muscle strength and speed of contraction. The same body positions required for perfect motion must be maintained in all strength work so that the transfer to performance is automatic. Otherwise, the rotations will be shut down, the stabilizers de-activated, and performance compromised. In addition, total muscle action will not be developed, and compensation creating over work of certain muscles, out of position, will cause injury.

Upper body development must ensure the correct positioning required of the upper body during movement as it works in conjunction with the hips to maintain balance and function in the correct plane. Therefore, chest, shoulder and upper back exercises must be performed in such a way that they maintain the stabilizers and develop the use of muscle order that will be used athletically. Otherwise, the strength attained will impede performance and lends to potential injury. In order to ensure that compensations are not taking over during strength training, the present systems and methods allow the athlete to see the lift as it is performed and grades the components that are essential to success.

In some embodiments, the feedback obtained from the movement training application may be used as an educational tool for both the athlete and the coaches/parents. The coaches or teacher (when applied to a classroom) may have access to all video, grading, and progress of each participant, so that it becomes documentation, tracking tool for them as well. In some embodiments, the movement training application also carries the ability for a coach to communicate with the athlete through his account, posting comments on performance, and for the athlete to submit understanding of his video analysis to the coach.

Through drill work on movement mechanics and functional strength development, the system develops each component that contributes to athleticism. Each piece provides the basis for speed. As running mechanics becomes more proficient, and functional strength improves, speed increases.

Computer Implementation

Figure 19A:
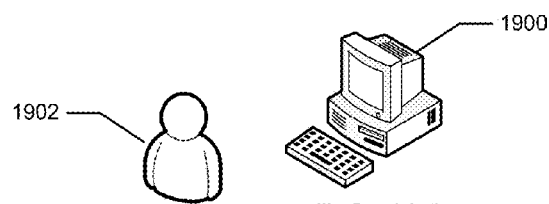
FIG. 19A is a block representation of a computer system and a user in accordance with one embodiment.

FIG. 19A illustrates a representation of a computer system 1900 and a user 1902. The user 1902 uses the computer system 1900 to perform performance training based on movement mechanics and functional strength development in an athlete. The computer system 1900 stores and executes a movement training application 1990.

Figure 19B:
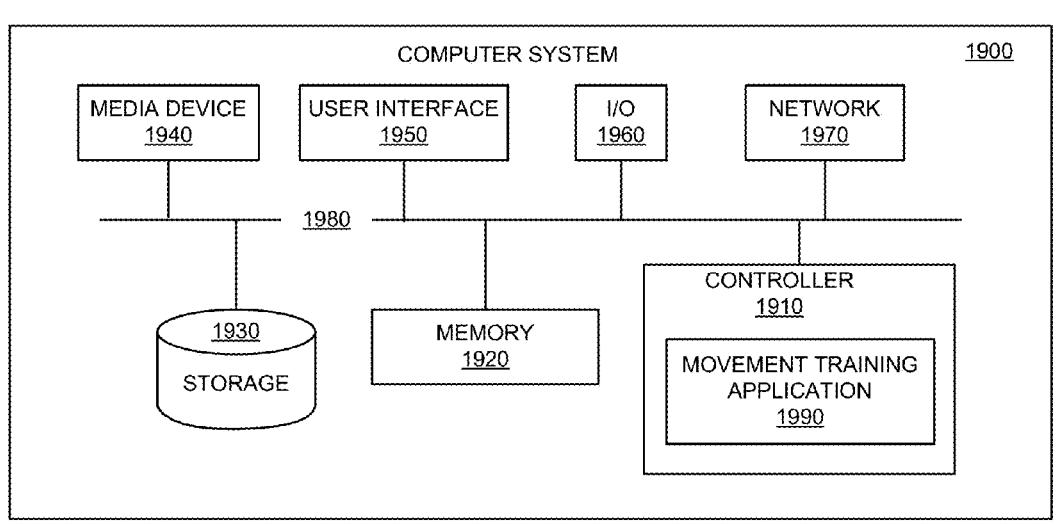
FIG. 19B is a functional block diagram illustrating the computer system of FIG. 18A.

FIG. 19B is a functional block diagram illustrating the computer system 1900 hosting the movement training application 1990. The controller 1910 is a programmable processor and controls the operation of the computer system 1900 and its components. The controller 1910 loads instructions (e.g., in the form of a computer program) from the memory 1920 or an embedded controller memory (not shown) and executes these instructions to control the system. In its execution, the controller 1910 provides the movement training application 1990 as a software system. Alternatively, this service can be implemented as separate hardware components in the controller 1910 or the computer system 1900.

Memory 1920 stores data temporarily for use by the other components of the computer system 1900. In one implementation, memory 1920 is implemented as RAM. In one implementation, memory 1920 also includes long-term or permanent memory, such as flash memory and/or ROM.

Storage 1930 stores data temporarily or long term for use by other components of the computer system 1900, such as for storing data used by the movement training application 1990. Such stored data may include previously measured athlete values. In one implementation, storage 1930 is a hard disk drive.

The media device 1940 receives removable media and reads and/or writes data to the inserted media. In one implementation, for example, the media device 1940 is an optical disc drive.

The user interface 1950 includes components for accepting user input from the user of the computer system 1900 and presenting information to the user. In one implementation, the user interface 1950 includes a keyboard, a mouse, audio speakers, and a display. The controller 1910 uses input from the user to adjust the operation of the computer system 1900.

The I/O interface 1960 includes one or more I/O ports to connect to corresponding I/O devices, such as external storage or supplemental devices (e.g., a printer or a PDA). In one implementation, the ports of the I/O interface 1960 include ports such as: USB ports, PCMCIA ports, serial ports, and/or parallel ports. In another implementation, the I/O interface 1960 includes a wireless interface for communication with external devices wirelessly.

The network interface 1970 includes a wired and/or wireless network connection, such as an RJ-45 or "Wi-Fi" interface (including, but not limited to 802.11) supporting an Ethernet connection.

The computer system 1900 includes additional hardware and software typical of computer systems (e.g., power, cooling, operating system), though these components are not specifically shown in FIG. 19B for simplicity. In other implementations, different configurations of the computer system can be used (e.g., different bus or storage configurations or a multi-processor configuration).

Methods of Movement Training

Figure 20:
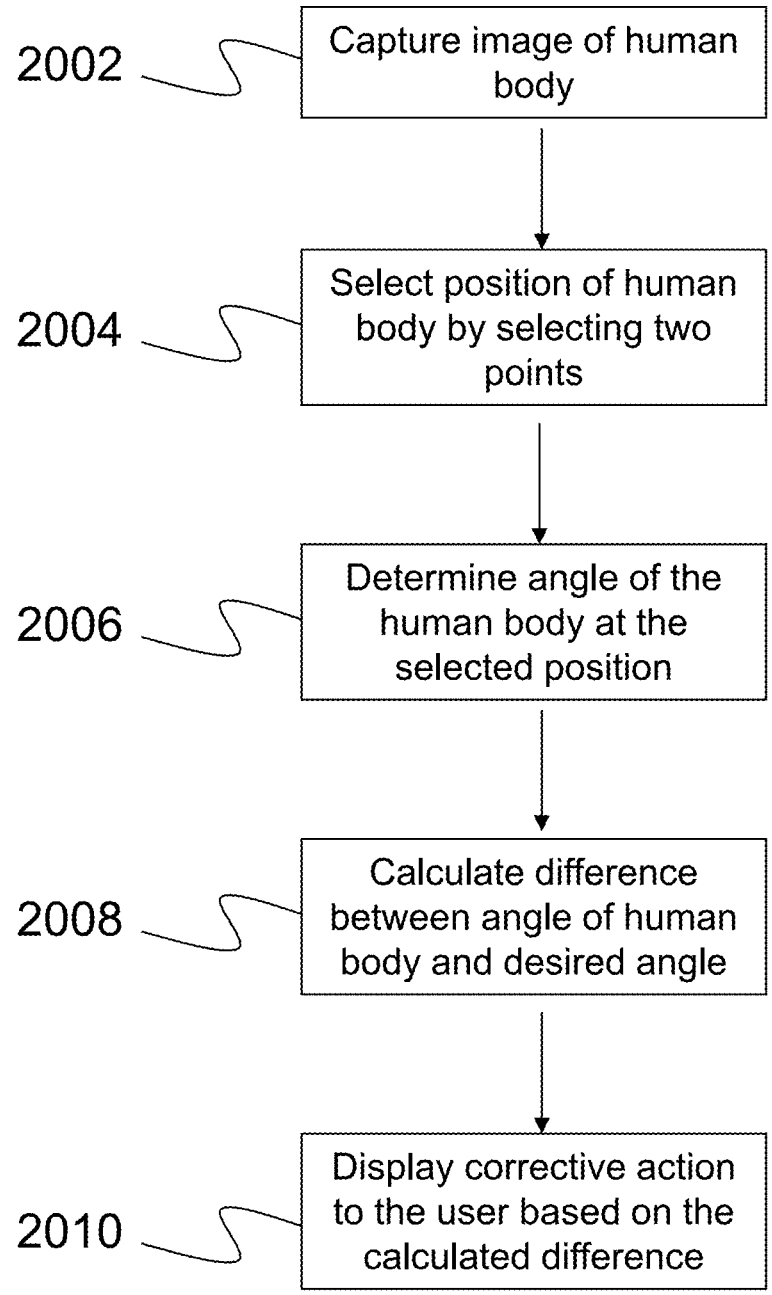
FIG. 20 is a flowchart which illustrates a method of movement training in accordance with one embodiment.

FIG. 20 is a flow chart which illustrates one embodiment of a method of training a human body. In a first step 2002, at least one image of a human body is captured. In step 2004, at least one position of the human body is selected on the captured image. The at least one position may be selected by selecting at least two points on the human body. In step 2006, an angle of the human body is determined at the at least one selected position. In step 2008, a difference is calculated between the angle at the selected position and a desired angle of the at least one selected position. In step 2010, a corrective action is displayed to the user based on the calculated difference.

Evaluating Performance Readiness

Figure 21:
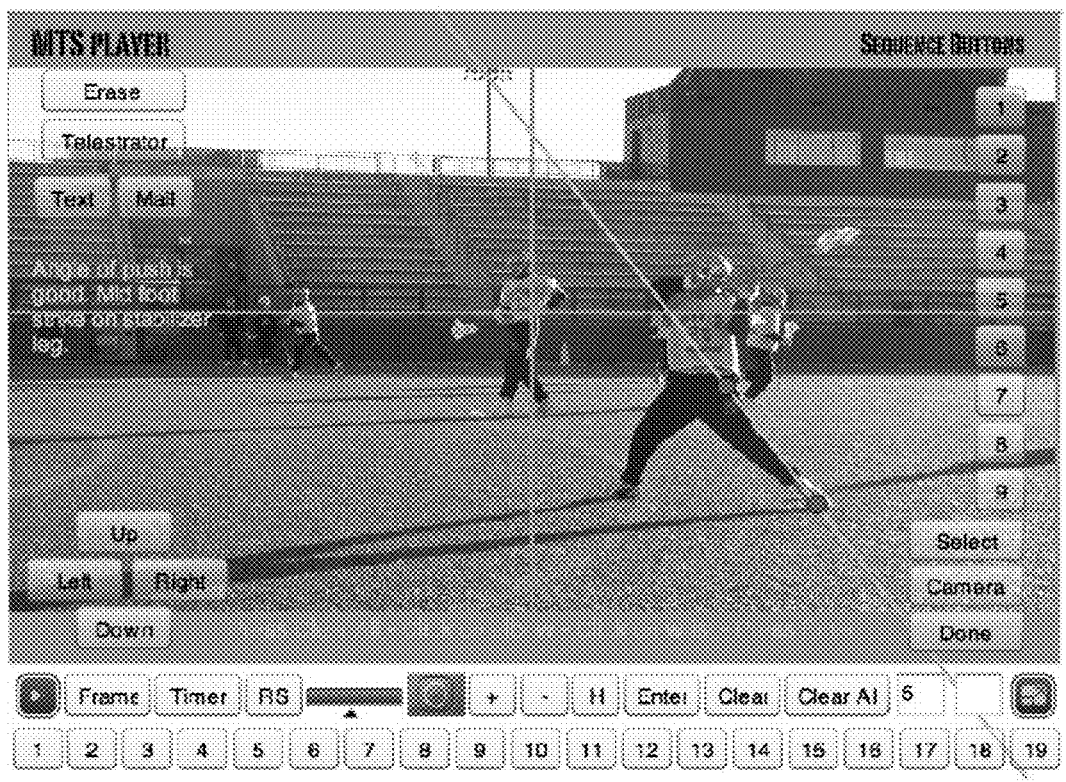
FIG. 21 is an image of a user interface for evaluating physical performance, in accordance with one embodiment.

In one embodiment, the systems and methods described above may be used to measure a user's technique during a physical activity, which along with a separate metric for strength or related ability, can be combined to provide an overall "performance ready" value. The performance ready value will indicate how ready the user is to perform the physical activity being evaluated, or if numerous physical activities are being evaluated, the user's overall ability to perform (such as in a particular sport). The performance ready score may be based on the combination of a technique score and a strength score, although other criteria relating to a user's physical ability and movement may be used, such as the movements described in the sections above. FIG. 21 illustrates an image of a user interface where a user's technique may be evaluated, as has been described above. In this image, the user in the image is being evaluated with regard to their technique of swinging a lacrosse stick. The specific technique being evaluated is the angle of the user's rear foot as it pushes off the ground while the user swings the lacrosse stick. Additionally, the angle of the user's leg is measured. These techniques can then be given values based on preset thresholds or amounts.

Figure 22:
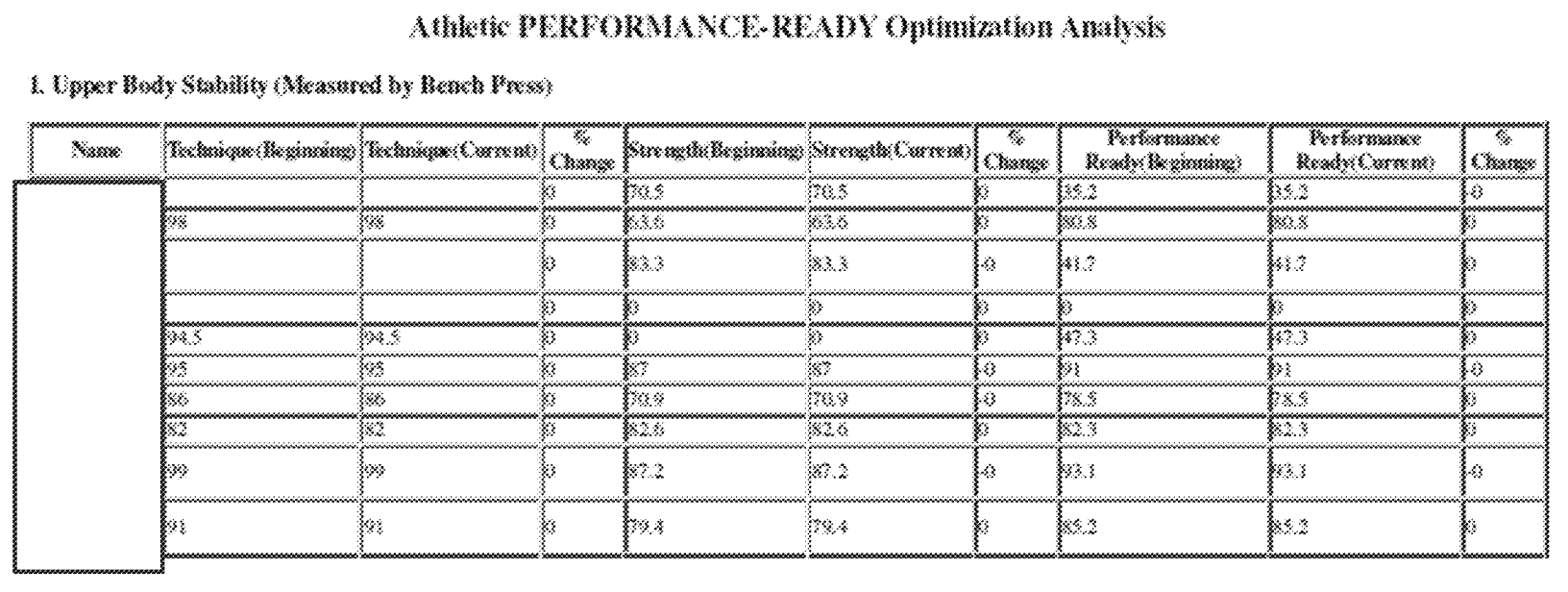

In one embodiment, the performance ready value is an average of a technique score and a strength score, as shown by the table in FIG. 22. In FIG. 22, a list of users on the left row (with names obscured for privacy) is provided, and subsequent columns on the right display numerical scores relating to past and present technique and a percentage of change over this time; scores relating to the user's past and present strength and a percentage of change over this time; and a past and present performance score and a percentage change over time. The performance score maybe a numerical average of the technique and strength scores, or it could be a weighted average where one of the criteria is weighted more heavily than another. This may occur if a particular activity is known to require more technique than strength, for example, in which case the technique value may be increased by a factor of a selected variable or simply increased by a specific amount. A percentage of change of the performance ready score over time may also be included, which may be the output that tells the user or a coach or trainer what the user's overall performance ability is and whether they are continuing to improve.

In FIG. 23, an overall performance ready table is shown, which displays a list of users' past and present scores that have been averaged across a number of different physical activities for which they were measured. For example, the overall performance ready score may be an average of five different physical activities which the user is completing. This overall performance ready score therefore provides a broader picture of a user's overall physical ability as opposed to just a particular type of physical activity. Thus, a coach, trainer or even the user may see if they are making progress based on an easy to understand numerical score.

In one embodiment, the performance score may be simplified to a number between 1 and 10, or it could be complex enough to require a larger ratings system, such as 1 to 100.

Applications of Performance Ready Evaluations

In one embodiment, the performance score may be utilized to measure a user's progress toward recovery from an injury. The user's progress may be measured based on their current and historical performance readiness values. In addition, if the user's performance ready score was determined prior to injury, this pre-injury performance ready value can be used as a benchmark to determine when the user has fully recovered from their injury.

In another embodiment, the performance ready scores may be monitored to look at trends that may be occurring across athletes of a same discipline or a group being trained with a particular technique or trainer. If the users in a particular group see a noticeable increase or decrease in their performance activity, the particular trainer, training sets, time spent training and other factors may be reviewed to determine the reason for the trending performance ready scores.

For example, if a group of users in a class or on a team see a universal drop in performance ready scores, it could be a sign that the users are being over-trained. This could be further confirmed by looking specifically at strength measurements for particular activities that the group is doing to see if their strength scores are also decreasing.

In another situation, if one user's performance ready score is flat or decreasing while other users in the same group are increasing, a coach or trainer can identify the abnormality and focus on that user to determine why they have not been progressing.

Another application of evaluating technique is in providing specific corrections to a user in order to improve their technique. In one embodiment, a user that receives a low score in technique for a particular activity may receive a message with a tip on how to correct the technique and improve their technique score. The message may include a hyperlink to a picture or video which demonstrates a proper technique, or even a hyperlink to the user's own video of their performance along with annotations that show why the user's technique is poor and how to correct it. An image of a messaging system which may be implemented is illustrated in FIG. 24. The messaging system may be provided to a coach or trainer who wants to communicate with their team or a specific athlete with regard to the performance ready scores that they are reviewing. The message interface may list one or more message senders, the message recipient(s), a brief summary of the message, and other pertinent information. The user may receive their own performance ready scores and other related scores in the message as well, so they can see their progress and identify their own trends.

Figure 25:
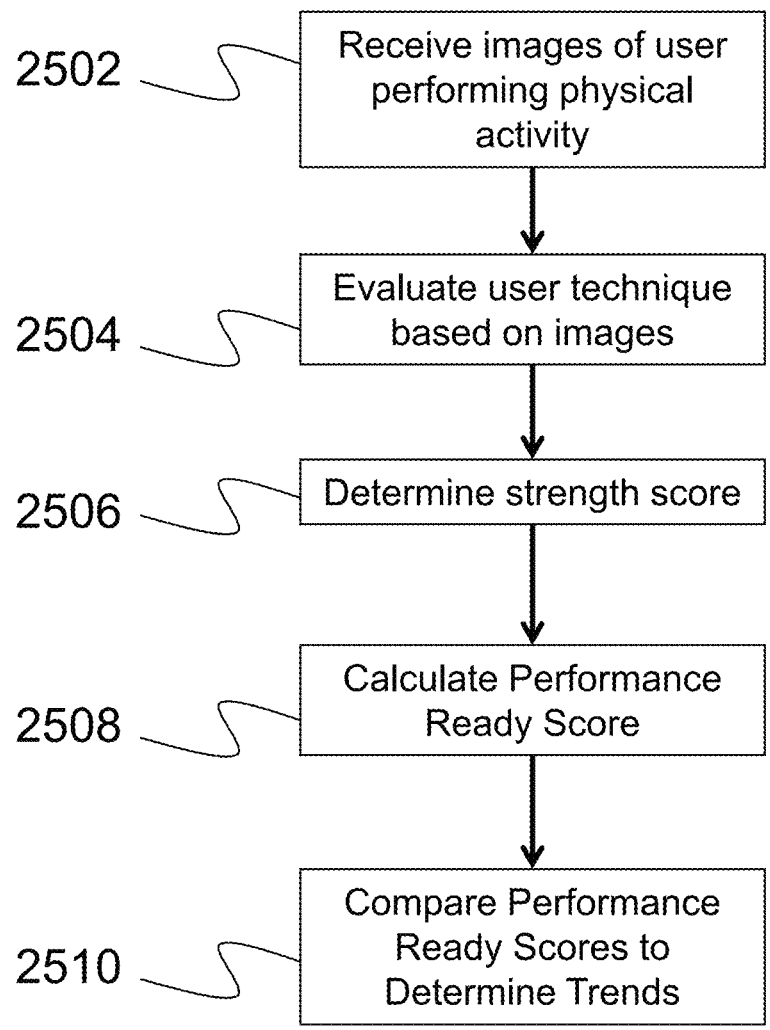
FIG. 25 is a flowchart illustrating a method of evaluating a physical activity of a user to determine a performance ready score, according to one embodiment.

FIG. 25 is a flowchart illustrating one embodiment of a method of evaluating a physical activity of a user to determine a performance ready score. In a first step 2502, one or more images of a user performing a physical activity are received for processing of the user's movement, as has been described herein. Using the images, a user's technique during the performance of the activity can be evaluated (such as the angle of the athlete's foot in FIG. 21). Based on the evaluation, the user's technique is assigned a numerical score. In step 2506, a strength score is determined based on data received with regard to the user's measured strength during the physical activity. Once the strength score and technique score are determined, these two scores are combined in step 2508 to generate a performance ready score. The technique and strength scores may be combined by averaging the two scores, summing the two scores, or weighting one or both of the scores individually before summing or averaging. The performance ready score can then be displayed to the user or another interested party in order to empirically assess the user's physical ability. In an additional step 2510, the performance ready score may be compared with past performance ready scores from the same user or with performance ready scores from other users in related groups, activities, teams, etc. to determine trends and patterns relevant to the user's training.

Movement Training Drills

One or more drills may be developed which focus on training a user to improve their movement, technique and overall performance readiness. Efficient movement is the common requirement of every sport, and teaching the body to create efficient movement is the basis for improving balance, coordination, timing, quickness, explosion and speed. Improving these athletic components allows an athlete to excel in the used of specific skills.

The system is developmental, and teaches the athlete how to use the feet effectively and then to assimilate that action throughout the rest of the body to produce synchronized action and reaction. This is done through a series of movement drills that address each component of movement and become more complex and inclusive as the athlete progresses.

The following is a list of drills divided up based on skill levels, starting with easier, Level I drills and finishing with more complex, Level IV drills.

Level I Drills

Walk and Press—Designed to acquaint the athlete with the mid foot and learn to use it as the base for all pushing motion to follow. It develops strength in the muscle use of the foot and lower leg, and teaches weight transfer, balance point, timing, body position and control. This drill is essential to the development necessary for performance of the more advanced drills. Perfecting it aids in the development of all areas of performance.

Ankle Snap—Furthers identification of the mid foot and its use as contact and balance point. Requires a quicker response from the muscles in the feet and lower leg to contact the ground at the correct point more quickly.

Ankle Bounce—Using the foot to initiate motion, further strengthens the mid foot and lower leg, while adding propulsion forward, requiring the body to take the action up throughout the legs and hips, and carry upper body position forward in a balanced motion.

Ankle Bounce Backward—Works on the coordination and timing of the upper and lower body together as the push backward coordinates with the release of the opposite side. It also helps develop balance over the mid foot, along with stability and control in carriage of the upper body.

Lateral Ankle Bounce—Addresses the ability to use the mid foot at a lateral angle, strengthening the use of the foot into inner leg, developing core strength to carry the body in balance as it moves laterally. Done correctly, this drill helps develop reactive ability in the feet to get on the ground quickly and in position under the hips.

Single Leg Firing—The beginning to the running component. The mid foot must control the initiation of movement, and the reaction off the ground resulting in a recovery position under the hips. We work one leg at a time to achieve learning of control and positioning on each side. It emphasizes foot use, timing, upper body carriage and positioning, arm action, hip strength and coordination.

Single Leg Firing Backward—Adds the component of balance to the process of using the foot quickly to fire upward, under the hip. Balance over the mid foot is important to carry the upper body backward in balance.

Single Leg Firing Laterally—Emphasizes the reactive use of the mid foot to move the body laterally while strengthening foot muscle use to achieve firing position under the hip.

Low Push Forward—Develops the use of the hips and hamstrings to maintain body position, while mid foot response generates forward motion, and responds rapidly to reestablish position with feet back under hips. Creates strength and coordination of upper and lower body working together to generate an explosive action, resulting in a balanced end point.

Low Push Zig Zag—Adds the component of using the mid foot in an angled direction to direct motion. Strength to hold upper body in position, while feet work at an angle is an additional component developed here, which is required in multiple sport skills applications. Feet must react first, then core ability must hold the upper body and hip position to take the body to the desired point as a unit.

Lateral Low Push—Strengthens the use of the foot in a lateral direction to push against the surface to move the rest of the body laterally. Requires even more core development to carry the upper body and hips simultaneously, and react with the push foot to regain position for the next move. Arm action connected with foot action is emphasized here as well.

Level II Drills

At this level, we work on creating turns while in motion. Drills that create stability in the center of the body allow movement to occur in balance. Positioning is taught here so that, at each foot strike, the upper body is in alignment with the mid foot. This is developed in every direction successively.

Bounce Push Out—Adds the component of extension through the push leg to produce power forward. Requires the feet to carry and contact at mid foot, absorbing more energy, and reacting rapidly as the body is covering more ground. Arm action is further expanded into a larger motion.

Bounce Push Out Backward—Using the same skills as before, now a greater effort from the foot is required, and the body has to carry in a level position as it moves backward a a faster rate, covering more ground. Further balance and coordination is developed within it.

Bounce Push Out Forward to Backward—Adds the complexity of turning, in stride, and continuing the same rate of motion in balance. Develops the ability of the body to maintain position, react across the foot to turn hips, land solidly on the next mid foot, and be able to continue speed of motion to the next turn. Several are performed in a row during the drill, handling back and forth turns off once side, then repeats using the other.

Lateral Bounce Push Out—emphasizes the push across the mid foot to direct the body in a lateral direction, but adds the component of extension as more ground is covered. The feet have to react more quickly to handle the increased energy, and still contact under the hips as the drill is performed. Arm action is performed in a larger range, as well, and coordinated with more rapid motion from the feet.

Lateral Bounce Side to Side—Full turn is required as the lateral bounce is performed to a change of direction that is initiated by the push across the mid foot, resulting in a turn of the hips, keeping balance, as the upper body follows hips, and the foot contact is in the correct position for the next push. Multiple turns are repeated in the course of the drill.

Firing Forward to Backward—continues the mechanics of the turn into the skill of firing, both forward and backward, requiring the foot use, balance, coordination, timing, quickness of mid foot response, hip position, and arm action. One foot is the primary focal point of the turn for multiple reps, then the other side is the active component. We train each side independently, to obtain unilateral proficiency.

Firing Lateral to Forward—A very quick drill, using the lateral push across the mid foot to create a rapid 90 degree turn, and the control to take the body back to the lateral position with balance and stability. This is repeated multiple times as it progresses, first with one foot being the turn foot, then with the other for multiple reps.

Firing Lateral to Backward—Requires the balance component to carry the body quickly into a backward position from a 90 degree turn, the quickness of the foot to get into the fire position going backward, and the rapid response across the foot to get the body back to a lateral position. This is repeated multiple times one side, then repeated multiple times on the other side. Thus further developing equal proficiency and strength on each side of the body.

Low Push Zig Zag (out two, back one)—Carrying the body forward in a 45 degree pattern, a stop must occur and a quick use of the outside foot to redirect action backward at 45 degrees is required. This works on the ability to position the body over mid foot at push, landing, and reversal, creating a balance point in each direction. The push foot is also required to react back into a position under the body immediately. Body components must remain intact as the whole body is moved as a unit from front to back, and front again. Multiple reps are repeated in a row.

Lateral Low Push (out two, back one)—while generating some power laterally, the body must be able to maintain low position, and land in a based position over the mid foot, even though it is moving laterally (upper body can't lean toward direction of motion, or against it) and mid foot must be able to react back the other direction rapidly, and with equal power. Arms must match foot action, and be able to reverse, creating coordination and synchronization. This applies directly to defensive efforts in many sports.

Low Push, alternating Forward to Backward (out two, back one)—Carrying the body forward, alternating off each foot, the second foot contact must react to push backward, without allowing the body to lean back, or reach with the other foot. This develops coordination, and quick reactive response with the feet. Balance throughout the drill requires the athlete to be in the correct body position, and be able to hold low position through the hips and hamstrings.

Zig Zag Low Push w Vert—Performing the zig zag low push while adding a vertical jump at last foot contact creates the ability to redistribute weight to the next motion and use the foot action to redirect the body into a vertical direction with quickness and power. Landing into a low position and producing another zig zag pattern requires the body to stabilize through the hips and hamstrings, and develops the immediate use of the foot to create the motion, in order to keep feet under the body, required for balance. Reactive strength and explosion are further enhanced by the vertical jump.

Lateral Low Push w Vert—Performing the lateral low push while adding a vertical jim at last foot contact creates the ability to redistribute weight to the next motion and use the foot action to redirect the body into a vertical direction with quickness and power. Landing into a low position and producing another lateral push, requires a rapid use of the mid foot to move the whole body laterally, and the coordination to push from one side while releasing the other simultaneously. Arm action must follow the timing of this drill, furthering coordination of the body as a unit. The vertical jump develops explosive strength and correct landing ability. (Furthering the running mechanics into Level II, we begin to coordinate firing from one side to the other)

Firing Two and Two—Firing the right leg for two reps, a bounce on each foot occurs followed by firing twice on the left, and is repeated in this pattern for several yards. The athlete learns to react through the mid foot from one side to the other in succession, requiring bilateral reactions and performance toward running Arm action must match up with foot action from side to side, and the body must be able to keep up on the bounce segment of the drill, requiring the feet to get on the ground quickly, and push quickly to set up the successive fire.

Firing One and One—Firing once on the right, followed by a bounce on each side, and another fire on the left, the athlete must respond form one side to other even more quickly, creating a bilateral motion similar to the run. Arms are quicker, foot strikes are sooner, and balance must be maintained to hold body position and keep feet under hips as movement occurs forward. Firing position and power of foot reaction is enhanced, as the fire occurs at its highest point under the hip.

Firing Right Bring in Left—Getting to top speed with right leg fire, halfway the left leg fires in with the right to match up and become a run. This develops the ability to maintain body position and arm action while firing at full speed. Precursor to running.

Build Up Run—Works on getting the body into the correct position and use of proper mechanics, and then builds speed off of that with increased arm action to increase the rate of foot strike along the way.

Sprints—Develops the rate of foot strike along with arm drive and power as the feet create extension through the hips, and body position is maintained.

Level III Drills

For Level III drills, at this level we combine components of the first two levels to further the development of coordination, and the ability to move in various directions with speed and power.

Bounce forward, break down, bounce backward, break down, back to forward again—This pattern repeats multiple times within a set, working on the ability to generate power, control body position to stop, and the foot reaction to maintain body position and reverse. Done at a quick pace. Assists in getting arm drive to begin rapidly as well.

Fire forward, break down, fire backward, break down, back to forward again—Advances the first step speed, body control and arm action. Done with each leg as the fire leg separately, with speed forward as a focus. This drill adds the fire component to the control and coordination required in the bounce.

Run to Backpedal, back to Run—Works on first step speed, body control to stop in balance, and the ability to maintain position by using the feet to reverse. This requires holding body position during the backpedal, being able to stop in balance again, and create immediate speed forward again. Repeated multiple times during the rep.

45 degree Sprints—A short sprint is run at a 45 degree angle. At the stop point, the outside foot must react across the mid foot at 45 degrees to begin the next sprint to the other side at 45 degrees. This continues forward along a designated distance, so that the outside foot on each turn must create a strong response to redirect the hips. All components of foot quickness, arm action, body position, hip strength, coordination and timing are required here, as well.

Firing×2 at 45 degree angles—Firing only the outside foot twice, followed by a balanced stop to a rapid fire twice on the other foot. Repeats multiple times along a prescribed distance. Teaches very rapid response, while requiring balance, body position, active foot strength, hip strength and arm coordination.

Firing×1 at 45 degree angles—The same drill but firing only once on each side, requiring an even quicker, more explosive response.

Firing 2 Side, Front, Back—Beginning with lateral fire, one leg fires twice, turns to forward, firing twice, to backward, firing twice, back to lateral—all on the same side. Multiple uses of the mid foot are required as the directions change, and the hips and upper body are carried together in the change. Performed at a quick pace. It is then reversed, going from lateral, to backward to forward, requiring a different foot use and hip carriage to get around.

Firing 1 Side, Front, Back—Same drill but using a single fire, which requires a more rapid assimilation, response, release of the opposite side, and balance as the turns occur.

L Drill—Various bouncing and running mechanics drills are performed on a lined surface where multiple stops and starts are performed at right angles. Emphasizes the ability to achieve the components of the drills with the addition of balanced stops and redirection with speed and quickness.

Low Push Zig Zag Doubles—The 45 degree low push is performed twice at the same angle, before switching to the opposite direction for two, then repeats. By pushing twice, the athlete must master an immediate weight shift and be able to create a quick response with the mid foot. Body position is important to have the balance required for the weight shift to happen at the right time.

Lateral Low Push to Forward Push—Lateral push off one side, to forward off the same side, back to lateral. This repeats along the distance. Requires coordination and balance to maintain weight over the mid foot to create the action. Performed separately on each side.

Lateral Low Push to Forward Push, switch sides—Same drill, but now after the forward push, the opposite foot must plant and create a quick motion to change the direction to a lateral push, then repeat to forward, etc.

Level IV Drills

Level IV Drills includes sport specific drills that take the abilities the athletes have developed to the next level. At this point, the athlete needs proficiency in the mechanics so that the skills are performed with balance, correct body positioning, stability, quickness, power, timing and speed. With this as a base, sport specific drills take the athleticism to the requirements of the respective sport. These drills are designed to replicate particular offensive or defensive actions that the athlete must perform.

Dodge Drill—Incorporates the low push at an angle, followed by a rapid fire through of the push foot. Repeats on the other side. Dodging requires a stable body position, the ability to push across the foot to direct the inside leg, while the push foot must be able to fire very rapidly to carry the body forward, past the defender.

Defensive Lateral Push—Uses the lateral low push, but adds an offensive opponent to react off of. The offensive player runs laterally, while the defensive player uses a powerful lateral push to stay with the offensive player. The offensive player reverses direction at a particular point, and the defensive player must react with the outside foot to redirect the push to match up. To cover a player, it is imperative that the defender is able to push from side to side, at one level. If he is up and down, too much time is spent in the air, and speed of movement is compromised. Feet must move quickly, in contact with the ground, and be under the body, in order to react quickly enough to cover an opponent.

Defensive Drop and Run—Uses the backward push and redirect across the mid foot to run at an angle. The offensive player runs toward the defender, who pushes back to give ground, making sure the weight distribution is over the outside foot, then immediately reacts across the mid foot to run at the same angle the offensive player has gone, in order to stay with him. In order to cover the opponent quickly enough to stay with him, the defender must be in a low, balanced position, and be able to react from the foot to direct the body. Timing is very important to enable the athlete to push back, and release on the other side at the same time, allowing him to cover ground, and still maintain body position. Then, the foot must be able to react across the mid foot to direct the hips into an angle to run with. The feet must also generate the run, supported by arm action to time the upper body with the feet.

Various illustrative implementations of the present invention have been described. However, one of ordinary skill in the art will see that additional implementations are also possible and within the scope of the present invention. As was noted above, the same principles can be applied to exercises, such as benching and squatting.

Accordingly, the present invention is not limited to only those implementations described above. Those of skill in the art will appreciate that the various illustrative modules and method steps described in connection with the above described figures and the implementations disclosed herein can often be implemented as electronic hardware, software, firmware or combinations of the foregoing. To clearly illustrate this interchangeability of hardware and software, various illustrative modules and method steps have been described above generally in terms of their functionality. Whether such functionality is implemented as hardware or software depends upon the particular application and design constraints imposed on the overall system. Skilled persons can implement the described functionality in varying ways for each particular application, but such implementation decisions should not be interpreted as causing a departure from the scope of the invention. In addition, the grouping of functions within a module or step is for ease of description. Specific functions can be moved from one module or step to another without departing from the invention.

We claim:

1. A method of assessing performance readiness of a human, comprising:
   receiving at least one image of a user performing a physical activity;
   evaluating a technique of the user's performance and determining a technique score based on the evaluation;
   determining a strength score based on the user's measured strength during the physical activity;
   combining the technique score and the strength score to generate a performance ready score; and
   displaying the performance ready score on a display.

2. The method of claim 1, further comprising determining the technique score by calculating an angle of the human body and finding a difference between the calculated angle and a desired angle.

3. The method of claim 1, wherein the performance ready score is generated by averaging the technique score and the strength score.

4. The method of claim 3, wherein at least one of the technique score and the strength score is weighted before averaging.

5. The method of claim 1, further comprising comparing the performance ready score with a previously calculated performance ready score to determine a change in performance readiness over time.

6. The method of claim 1, further comprising comparing the performance ready score with at least one other performance ready score from at least one other user to determine a user's performance readiness in relation to the at least one other user.

7. The method of claim 6, wherein the at least one other user is a member of a group to which the user belongs.

8. The method of claim 1, further comprising communicating a corrective action to the user if the technique score does not meet a threshold value.

9. A method of assessing a physical rehabilitation process of a human, comprising:
   generating a first performance ready score for a user, wherein the performance ready scores measures an ability of a user to perform a physical activity;
   generating a second performance ready score for the user after the user has been physically impaired or injured;
   comparing the first performance ready score and the second performance ready score to determine a difference between the first performance ready score and the second performance ready score;
   determining a progress of a rehabilitation process of the user based on the determined difference.

* * * * *